(12) United States Patent
Tanaka et al.

(10) Patent No.: US 9,072,601 B2
(45) Date of Patent: Jul. 7, 2015

(54) INTRAOCULAR LENS INSERTION DEVICE

(75) Inventors: Masayoshi Tanaka, Nagoya (JP);
Kazuharu Niwa, Nagoya (JP);
Yasuhiko Suzuki, Hashima-gun (JP)

(73) Assignee: KOWA COMPANY, LTD., Nagoya (JP)

( * ) Notice: Subject to any disclaimer, the term of this patent is extended or adjusted under 35 U.S.C. 154(b) by 449 days.

(21) Appl. No.: 13/502,637

(22) PCT Filed: Oct. 22, 2009

(86) PCT No.: PCT/JP2009/005546
§ 371 (c)(1),
(2), (4) Date: May 7, 2012

(87) PCT Pub. No.: WO2011/048631
PCT Pub. Date: Apr. 28, 2011

(65) Prior Publication Data
US 2012/0221102 A1 Aug. 30, 2012

(51) Int. Cl.
*A61F 2/16* (2006.01)
*A61F 2/14* (2006.01)

(52) U.S. Cl.
CPC . *A61F 2/167* (2013.01); *A61F 2/16* (2013.01); *A61F 2/1648* (2013.01); *A61F 2/1662* (2013.01); *A61F 2/143* (2013.01); *A61F 2002/1681* (2013.01)

(58) Field of Classification Search
CPC ............. A61F 2/16; A61F 2/1648; A61F 2/1662–2/1678; A61F 2/1691; A61F 2/143; A61F 2002/1681
See application file for complete search history.

(56) References Cited

U.S. PATENT DOCUMENTS

| | | | | |
|---|---|---|---|---|
| 6,491,697 B1 * | 12/2002 | Clark et al. | | 606/107 |
| 7,037,312 B2 * | 5/2006 | Kikuchi et al. | | 606/107 |
| 7,156,854 B2 | 1/2007 | Brown et al. | | |

(Continued)

FOREIGN PATENT DOCUMENTS

CN 101467925 A 7/2009
EP 2 298 242 A1 3/2011

(Continued)

OTHER PUBLICATIONS

Jan. 26, 2010 International Search Report issued in International Patent Application No. PCT/JP2009/005546 (with translation).

(Continued)

*Primary Examiner* — Jonathan W Miles
*Assistant Examiner* — Todd J Scherbel
(74) *Attorney, Agent, or Firm* — Oliff PLC

(57) ABSTRACT

An intraocular lens insertion device having a novel configuration, capable of more accurately arranging front and back surfaces of an intraocular lens in a proper direction. The intraocular lens insertion device is adapted in such a manner that the intraocular lens is set on a stage in a state placed flat with a pair of haptics extended facing front and back sides in a movement direction by a plunger. Also, an interfering acting part is provided to an insertion tube part, and the interfering acting part interferes with the haptic, which is extended facing the front side in the movement direction of the intraocular lens moved by the plunger, to apply on the haptic an external force toward the back side in the movement direction. Thus, the interfering acting part curves and deforms the haptic to a side approaching an optical portion.

5 Claims, 22 Drawing Sheets

(56) References Cited

U.S. PATENT DOCUMENTS

| | | | |
|---|---|---|---|
| 8,273,122 B2 * | 9/2012 | Anderson | 623/6.12 |
| 8,702,794 B2 * | 4/2014 | Hoffmann et al. | 623/6.12 |
| 2007/0270881 A1 | 11/2007 | Hishinuma et al. | |
| 2008/0033449 A1 | 2/2008 | Cole et al. | |
| 2009/0171366 A1 | 7/2009 | Tanaka | |
| 2011/0082463 A1 | 4/2011 | Inoue | |
| 2012/0221102 A1 * | 8/2012 | Tanaka et al. | 623/6.12 |

FOREIGN PATENT DOCUMENTS

| | | |
|---|---|---|
| JP | A-2003-070829 | 3/2003 |
| JP | A-2004-351196 | 12/2004 |
| JP | A-2005-110924 | 4/2005 |
| JP | 2007-307082 A | 11/2007 |
| JP | A-2009-160151 | 7/2009 |
| JP | A-2009-160153 | 7/2009 |
| WO | WO 2009/148091 A1 | 12/2009 |

OTHER PUBLICATIONS

Office Action issued in Chinese Patent Application No. 200980162060.0 dated Jan. 13, 2014 (with translation).

May 15, 2012 International Preliminary Report on Patentability issued in International Patent Application No. PCT/JP2009/005546.

Extended Search Report issued in European Patent Application No. 09850532.4 dated May 16, 2014.

Oct. 31, 2014 Office Action issued in JP Application No. 2013-243379.

* cited by examiner

FIG.7
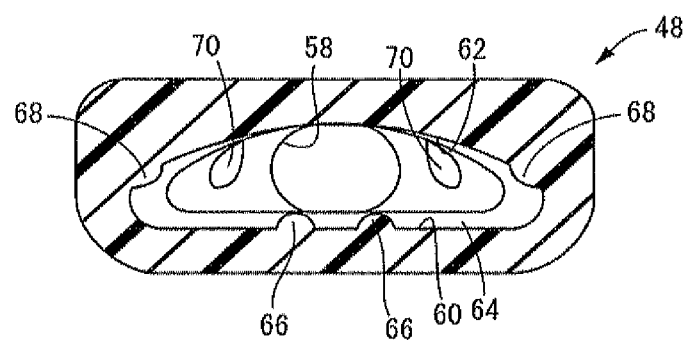
A—A
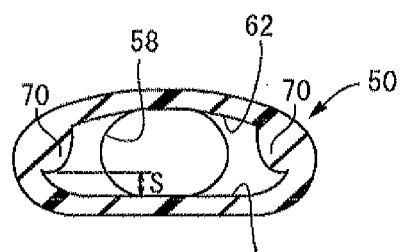
B—B
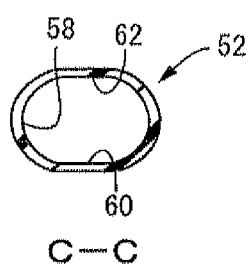
C—C

FIG.13
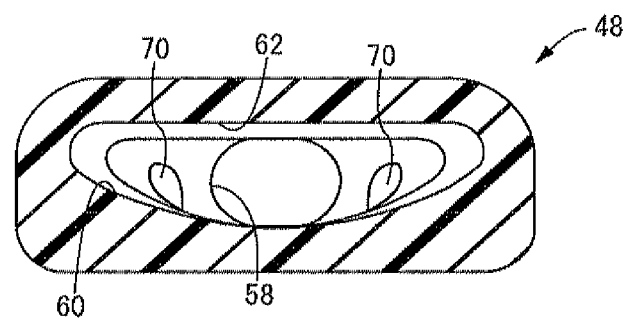
A—A
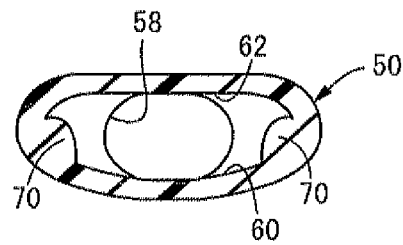
B—B
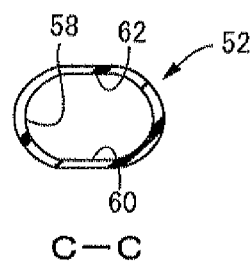
C—C

INTRAOCULAR LENS INSERTION DEVICE

TECHNICAL FIELD

The present invention relates to an intraocular lens insertion device used for inserting an intraocular lens into the eye.

BACKGROUND ART

From the past, with cataract surgery and the like, a method has been used for which the intracapsular crystalline lens is extracted through an incision provided in ocular tissue such as the cornea (sclera) or anterior capsule of the lens or the like, and after removal, an intraocular lens substituted for that crystalline lens is inserted into the eye using that incision, and arranged within the capsule.

With this intraocular lens surgical operation method, there has been used an intraocular lens insertion device as noted in Patent Document 1 (Published Unexamined Japanese Patent Application JP-A-2003-70829) and Patent Document 2 (Published Unexamined Japanese Patent Application No. JP-A-2004-351196). With these intraocular lens insertion devices, the insertion tube part provided at the tip of the device main unit is made to be inserted and enter into the eye through the eye incision, and in a state with the intraocular lens deformed to be smaller within the device main unit, it is made to be extruded into the eye from the tip opening of the insertion tube part. Then, the intraocular lens is arranged within the capsule by the intraocular lens which was extruded into the eye expanding by its own restoration force within the capsule. If this kind of intraocular lens insertion device is used, it is possible to keep the incision small, making it possible to reduce the trouble required for the surgical operation and also possible to reduce the occurrence of postoperative astigmatism and the risk of infection.

However, many intraocular lenses are regulated in terms of the lens front-back direction, requiring that the lens front-back surface is set correctly for arrangement within the capsule. The reason for regulating the lens front-back direction is because there are items for which a haptic is tilted toward the lens front surface (cornea side) so that the optical portion is pressed on the inner surface of the back part (vitreous body side) of the crystalline capsule with the purpose of inhibiting secondary cataracts and the like.

However, when a surgical operation is done using the prior art intraocular lens insertion device, there was the problem that the intraocular lens extruded into the eye easily deployed within the capsule with the front-back surfaces inverted. Reinverting an intraocular lens which has deployed inverted within the capsule in this way into the proper direction within the capsule after surgery is very difficult. Therefore, the practitioner needs to do a special operation such as trying to insert the intraocular lens with the insertion device displaced in the rotation direction by the amount it is assumed the intraocular lens will be inverted in advance, or rotating the insertion device at the moment the intraocular lens is extruded from the insertion device and expands within the capsule. Naturally, this kind of work requires skill and is not easy in either case. In particular, rotating an insertion tube part that has been inserted in the eye requires work to be done carefully so as not to cause damage to biological tissue such as the eye incision or the like, and there was the problem that this was a heavy burden on the practitioner.

BACKGROUND ART DOCUMENTS

Patent Document

Patent Document 1: JP-A-2003-70829
Patent Document 2: JP-A-2004-351196

SUMMARY OF THE INVENTION

Problem the Invention Attempts to Solve

The present invention has been developed in view of the circumstances described above as the background, and it is one object of the present invention to provide an intraocular lens insertion device with a novel constitution, which makes it possible to do the surgical operation of inserting the intraocular lens into the eye with the front and back surface of the intraocular lens facing the proper direction more reliably and easily.

Means for Solving the Problem

To address the problem noted above, as the result of a great deal of earnest study, the inventors recognized that the cause of the lens inversion was the expansion operation of the intraocular lens within the capsule with the haptic tip as the constraint center.

Specifically, with the prior art intraocular lens insertion device, with an intraocular lens that has been folded to be small within the insertion tube part, a pair of haptics projecting from the optical portion are made to extend in the front-back direction in the delivery direction. This is to avoid having the optical portion and the pair of haptics fold over each other of, making it possible to extrude from a smaller cross section insertion tube part, so that the eye incision can be smaller. Furthermore, the pair of haptics extending in the front-back direction of the optical portion are made to be extruded in a state extending actively in the front-back direction. This is because if the haptic bends sharply, there is the risk that there will a hindrance to expansion and restoration within the capsule due to residual stress and a crazing phenomenon (entry of minute cracks).

One of the haptics extending forward in the extrusion direction from the optical portion during insertion into the eye in this way is delivered from the tip opening of the insertion tube part and projects into the capsule ahead of the optical portion, and at the stage at which the optical portion is delivered into the capsule, the haptic is already in contact with the intracapsular surface. Meanwhile, the intraocular lens delivered into the capsule is rounded to be small within the insertion tube part as noted in Patent Document 1, for example. Because of that, the haptic extending out from the outer periphery part of the optical portion is extruded from the insertion device in an inverted state, and there were many cases of being in contact with the intracapsular surface in a state inverted from the proper position. Then, by the optical portion expanding with the contact point of the haptic delivered first on the intracapsular surface being the constraint center, in the wake of the haptic which contacted the intracapsular surface being in an inverted state, it became possible to anticipate items for which the optical portion would be inverted and expanded within the capsule. In light of that, the inventors completed the present invention based on those new findings.

A first mode of the present invention provides an intraocular lens insertion device comprising: a tube shaped device main unit arranged in which is set an intraocular lens having a pair of haptics projecting from an optical portion; a plunger adapted to be inserted into the device main unit from a back side in an axial direction thereof and attached to the device main unit; a stage arranged on which the intraocular lens is set being provided in an intermediate part of the axial direction of the device main unit; and a tapered insertion tube part formed facing a front side in the axial direction from the stage so that the intraocular lens set on the stage is able to be inserted into an eye by being moved in an axial front direction of the device main unit by the plunger and by being transformed to be smaller and extruded through the insertion tube part, the intraocular lens insertion device being characterized in that: the stage is arranged such that the intraocular lens is able to be on the stage in a state placed flat, and the pair of haptics are set in a state extended facing front and back sides in a movement direction by the plunger, and in the insertion tube part, provided is an interfering acting part that is adapted to be in contact with the haptic extended facing the front side in the movement direction of the intraocular lens moved by the plunger, and apply external force on the haptic toward the back side in the movement direction, in order to curve and deform the haptic to a side approaching the optical portion.

According to the intraocular lens insertion device of this mode, when moving the intraocular lens set on the stage in the front direction of the device main unit using the plunger, one of the haptics extending to the front from the optical portion is actively curved and deformed to the optical portion side by the interfering action on the interfering acting part. As a result, when the intraocular lens is extruded from the tip opening part of the insertion tube part of the device main unit, there is inhibition of the front haptic extending to the front from the optical portion and projecting a great deal, and the projection volume to the front of the haptic from the optical portion is kept small. With this arrangement, when the optical portion is deployed and deformed within the capsule after extrusion from the insertion tube part, having the haptic press against the intracapsular surface ahead of deploying of the optical portion is avoided, or the contact force of the haptic pressing against the intracapsular surface ahead of deployment of the optical portion is made smaller. Therefore, when deploying the optical portion, it is possible to avoid rotation of the optical portion with the pressing point of the haptic on the intracapsular surface as the center, and as a result, optical portion inversion of the intraocular lens during insertion into the eye is effectively prevented.

Then, since it is possible to prevent optical portion inversion during insertion into the eye in this way, it is no longer necessary to do a high level skilled operation such as rotating the intraocular lens insertion device when doing a surgical operation, so the surgical operation work is easier, and a reduction in burden for the practitioner as well as a decrease in operational errors is achieved. Also, for the patient as well, when having an operation, a reduction in the invasiveness of the wound as well as a reduction in the risk burden are achieved.

A second mode of the present invention provides the intraocular lens insertion device according to the first mode, wherein the interfering acting part of the insertion tube part is constituted by an engaging part formed at least at one side in a width direction of the insertion tube part and arranged to engage with the haptic of the intraocular lens moving within the insertion tube part.

With the intraocular lens insertion device of this mode, the engaging part is formed as the interfering acting part on the width direction end part side, avoiding the width direction center part of the insertion tube part. Because of that, even when the intraocular lens placed on the stage is deformed to be small by the insertion tube part and extruded, the engaging part is formed avoiding the center part of the insertion tube part at which it is assumed that the optical portion of the intraocular lens will pass through, and adverse effects by the engaging part on the optical portion are avoided. Preferably with this mode, the gradually contracting cross section part at the entry side of the insertion tube part connected from the stage is a flat cross section shape that widens in the width direction of the stage. Then, the engaging part is provided on at least one side in the width direction of the gradually contracting cross section part having this flat cross section shape.

Also, the engaging part of this mode preferably is formed on both sides in the width direction of the insertion tube part. By doing this, for example when a pair of haptics are formed extending in a "J" character shape curving to one side in the peripheral direction from the optical portion, specifically when the pair of haptics extending to both sides of the optical portion overall form an "S" character shape, it is possible to realize an engaging part which can act in the same way in any direction that the haptic extends from the optical portion.

Furthermore, the engaging part with this mode is preferably constituted by convex parts or projections, or concave parts noted as the third through sixth modes noted below.

A third mode of the present invention provides the intraocular lens insertion device according to the second mode, wherein the engaging part is constituted by a convex part projecting above the inner surface at least at one side of the width direction of the insertion tube part.

A fourth mode of the present invention provides the intraocular lens insertion device according to the third mode, wherein the convex part noted in the third mode is constituted by a flexible locking piece that is deformable in the direction for which a projection height of the flexible locking piece gets smaller above the inner surface of the insertion tube part opposite to a projection direction of the flexible locking piece above the inner surface of the insertion tube part.

A fifth mode of the present invention provides the intraocular lens insertion device according to the third or fourth mode, wherein a flat bottom surface extending from the stage is provided at an opening part to the stage side of the insertion tube part, and the convex part is formed at a position separated upward from the bottom surface at least at one side of the width direction of the bottom surface, and a gap is provided further to the bottom surface side than the convex part.

Furthermore, a sixth mode of the present invention provides the intraocular lens insertion device according to the second mode, wherein the engaging part is constituted by a concave part that opens to the inner surface at least at one side of the width direction of the insertion tube part.

With any of these third through sixth modes as well, the engaging part of the second mode can be constituted, but in particular according to the fourth mode, when the intraocular lens is extruded through the insertion tube part, when passing through an optical portion with a large capacity, by the flexible locking piece being pressed and deformed by the optical portion, the projection height of the flexible locking piece deforms to be smaller above the inner surface of the insertion tube part. Therefore, while an effective engaging action is exhibited in relation to the front haptic with a capacity smaller than the optical portion, and the haptic is curved facing the back, deformation occurs so as to escape within the insertion tube part in relation to the optical portion, a problem such as catching of the flexible engaging piece on the optical portion is prevented, and it becomes possible to make it easy for the optical portion to pass through the insertion tube part.

Also, with the fifth mode, at the bottom surface of the insertion tube part to which the intraocular lens is sent from the stage, the convex part formed near the width direction edge part is formed separated upward from the bottom surface, and even at that convex part forming position, a large width direction dimension of the bottom surface of the insertion tube part is ensured. Accordingly, at the width direction both sides edge parts of the bottom surface of this insertion tube part, the outer peripheral edge part of the optical portion of the intraocular lens that was sent smoothly over the bottom surface escapes being made to pass through the gap provided below the convex part, and problems such as catching of the optical portion on the convex part are reduced or avoided.

Furthermore, with the sixth mode, by providing a concave part that opens to the inner surface of the insertion tube part, the engaging part that engages with the haptic of the intraocular lens can be constituted using the opening edge part of this concave part. In this way, by using the opening edge part of the concave part, it is possible to provide an engaging part as an interfering acting part while avoiding or keeping small the projection to the inner periphery surface of the insertion tube part, so a decrease in the cross section area of the insertion tube part is avoided or reduced, and an engaging part which makes it possible to avoid adverse effects on the passage of the optical portion can be realized.

A seventh mode of the present invention provides the intraocular lens insertion device according to the first mode, wherein the interfering acting part of the insertion tube part is constituted by a rough surface part provided on an area for which the haptic of the intraocular lens moving within the insertion tube part contacts the inner surface of the insertion tube part.

With this mode, when the intraocular lens is moved to the front within the insertion tube part, the frictional resistance to the haptic becomes greater due to the rough surface part, and the haptic is curved to the back based on that frictional resistance, and is deformed toward the optical portion side. By using frictional resistance by the rough surface part in this way, it is possible to realize an interfering acting part for which it is possible to apply external force toward the back side in relation to the haptic while suppressing the projection volume of the interfering acting part, and in some cases with the interfering acting part not projecting from the internal peripheral surface of the insertion tube part at all. Then, by making the projection volume of the interfering acting part to the insertion tube part inner peripheral surface smaller, it is possible to avoid problems such as the interfering acting part catching on the optical portion that is extruded through the insertion tube part.

An eighth mode of the present invention provides the intraocular lens insertion device according to the first mode, wherein the interfering acting part of the insertion tube part is constituted by a flexible projection which is formed at least at one side of a height direction of the insertion tube part and arranged to engage with the haptic of the intraocular lens moving within the insertion tube part, and a projection volume of the flexible projection to the insertion tube part interior is made smaller by deformation after engagement, allowing passage of the optical portion of that intraocular lens.

With the flexible projection constituting this mode, it is possible to make a secure engagement with the haptic by projecting to a large degree into the insertion tube part when engaging the haptic, and also to make the projection volume to the insertion tube part interior small when the optical portion is passing through, allowing movement of the optical portion without hindrance. In particular, this flexible projection is pressed by contact of the haptic and deformed, so the haptic is effectively engaged even in the deformed state, and it becomes possible to more reliably curve and deform the haptic toward the optical portion.

A ninth mode of the present invention provides the intraocular lens insertion device according to the first mode, wherein the interfering acting part of the insertion tube part is constituted by an entry contact member made to be entered into a hollow interior of the insertion tube part, and made to contact the haptic of the intraocular lens moving within that insertion tube part, and also after the haptic is deformed by the entry contact member contacting on the haptic, an entry volume of the entry contact member to the hollow interior of the insertion tube part is made smaller, allowing the movement of the intraocular lens through the insertion tube part.

The entry contact member that constitutes this mode can be made to greatly project in the insertion tube interior when interfering with the haptic and curving the haptic, and can also be made to allow smooth passage of the optical portion by making the projecting height smaller in the insertion tube part interior when the optical portion passes through that projection site. In particular, since the projection height in the insertion tube part interior can be adjusted, it is possible to suitably adjust to be able to realize both the interfering action on the target haptic and allowing passage of the optical portion according to the properties of the used intraocular lens, lubricating agent and the like. Also, during passing through of the optical portion, by extracting the entry contact member from the insertion tube part or making the tip surface of the entry contact member flush with the inner surface of the insertion tube part, it is possible to completely avoid adverse effects of the entry contact member in relation to passage of the optical portion.

A tenth mode of the present invention provides the intraocular lens insertion device of any one of the first through ninth modes, wherein the constitution is such that in the hollow interior of the insertion tube part, provided is a deformation guide member by which the optical portion of the intraocular lens is folded and deformed in a mountain shape or valley shape for which the optical portion is convex in either one of an upward or downward direction using a ridge line or valley line extending in the movement direction along with the movement within the insertion tube part with interference on the intraocular lens being made to move within the insertion tube part, and on an interfering surface that interferes with the haptic on the interfering acting part provided on the insertion tube part, a tilt is added that tilts gradually toward a concave side that faces opposite a convex side of the optical portion deformed by the deformation guide member as the interfering surface moves forward in the movement direction of the intraocular lens, and by guiding action of the tilt added to the interfering surface, the haptic is deformed and guided to enter facing the concave side of the optical portion of the folded and deformed intraocular lens.

With this mode, since a tilt is given to a specific direction on the interfering surface of the interfering acting part, while the haptic pushed from the back in relation to this interfering surface is pushed toward one surface side which will be the concave side of the deformed optical portion along the tilt of the interfering surface, it is curved and deformed in the direction approaching toward the optical portion. As a result, even in a case when the haptic extending to the front overlaps near the optical portion, it is possible to effectively prevent problems such as the intraocular lens extrusion resistance becoming too large due to the haptic riding above the convex side of the curved and deformed optical portion, and being strongly sandwiched between the inner peripheral surface of the insertion tube part and the convex side surface of the optical portion. In other words, it is easy for a gap to appear on the concave side in comparison with the convex side of the curved and deformed optical portion, the haptic is successfully entered into this gap, and it is possible to keep the intraocular lens extrusion resistance small while maintaining the curved state of the haptic.

In particular, by the tip of the haptic being entered into the gap that exists in the concave side of the curved and deformed optical portion, it is possible to realize tucking that uses the optical portion to hold the haptic so as to be embraced in a curved state. Then, by actively causing this kind of tucking, with the intraocular lens extruded into the capsule from the tip opening part of the insertion tube part, it is possible to hold the curved state of the haptic more reliably until the optical portion starts expanding, and it is possible to more effectively inhibit the inversion of the optical portion within the capsule thought to be due to the projection of the haptic that comes ahead of the optical portion.

An eleventh mode of the present invention provides the intraocular lens insertion device of any one of the first through tenth modes, wherein the intraocular lens set on the stage is constituted as one piece for which the pair of haptics are formed integrally with the optical portion.

Specifically, the present invention can also of course be applied to intraocular lens insertion devices such as of a three piece constitution or the like whereby a haptic formed separately from the optical portion is attached later to the optical portion, but in particular, it is preferable to apply it to an intraocular lens insertion device used for doing insertion surgery of an intraocular lens of a one piece constitution as noted in this mode. After all, with an intraocular lens of a one piece constitution, the haptic is formed with the same soft material as the optical portion, so compared to intraocular lenses with a three piece constitution for which there are many cases of the haptic being formed from a harder material than the optical portion, the haptic elastic restoring force is smaller, and the haptic cross section area is larger. Because of that, with an intraocular lens of a one piece constitution for which the cross section area of the haptic, particularly the haptic thickness dimension, is greater than the thickness dimension of the outer periphery edge part of the optical portion, it is possible to easily form an interfering acting part which can apply curved external force by engaging with the haptic while avoiding adverse effects such as catching on the optical portion. In fact, since the haptic restoration (expansion) speed with the intraocular lens extruded from the insertion tube part is also suppressed, even if the curve volume of the haptic isn't all that big, there is a reduction or avoidance of pressing on the capsular interior by the haptic ahead of the expansion of the optical portion, so it is possible to avoid inversion of the optical portion inside the capsule.

Effect of the Invention

With the present invention, when moving the intraocular lens forward within the insertion tube part, the interfering acting part interferes with the haptic, the haptic is curved and deformed at the side approaching the optical portion, and it is possible to keep the haptic projection volume from the optical portion small when extruded from the insertion tube part into the eye. By doing this, it is possible to reduce or avoid projection of the haptic and pressing against intraocular tissue ahead of the intraocular lens being extruded from the insertion tube part and expanding. As a result, it is possible to prevent inversion of the optical portion within the eye during expansion which is thought to occur with the pressing point by the haptic on the intraocular tissue as the focus.

BRIEF DESCRIPTION OF THE DRAWINGS

FIG. 7 is an A-A through C-C cross section view of FIG. 5.

FIG. 13 is a transverse section for explaining another mode of the deformation guide member that can be applied with the present invention, and is the A-A through C-C cross section of FIG. 5.

EMBODIMENTS FOR CARRYING OUT THE INVENTION

Embodiments of the present invention will be explained below with reference to attached drawings.

Figure 1:
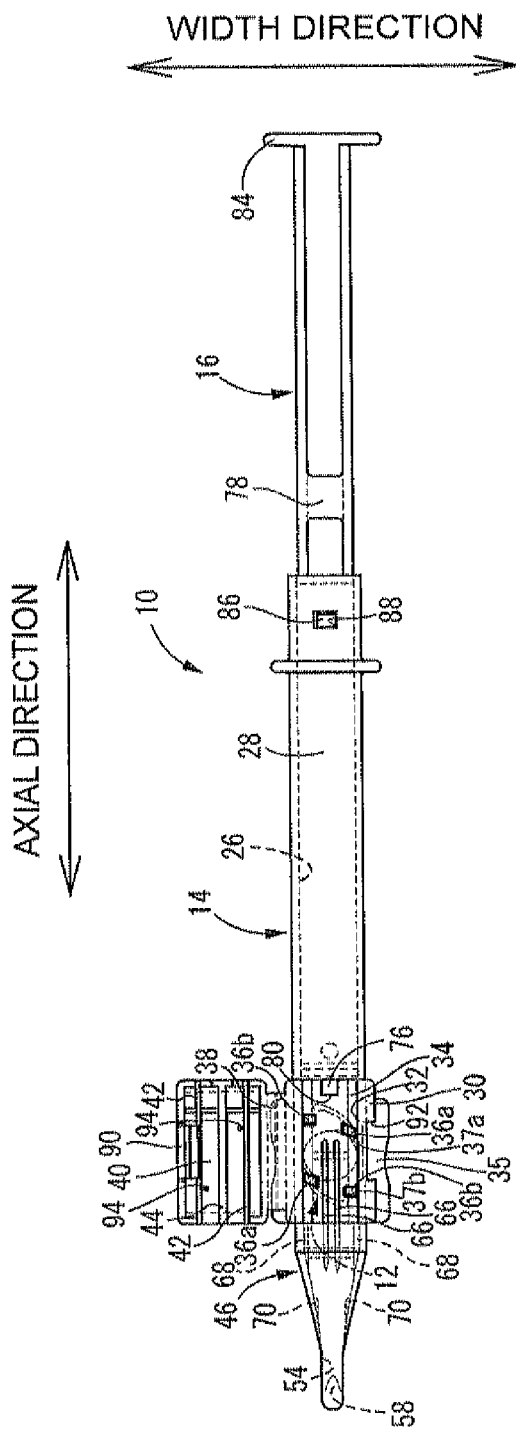
FIG. 1 is a plan view of an intraocular lens insertion device as a first embodiment of the present invention.
Figure 2:
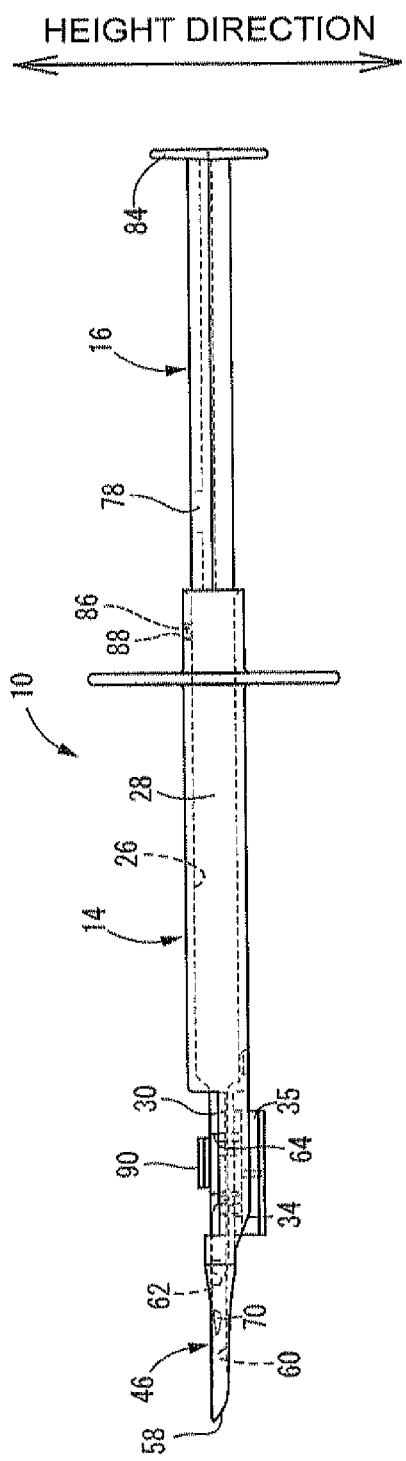
FIG. 2 is a side view of the intraocular lens insertion device shown in FIG. 1.

FIG. 1 and FIG. 2 show an intraocular lens insertion device 10 as a first embodiment of the present invention. The intraocular lens insertion device 10 is constituted with a plunger 16 attached pressed in against a roughly tube shaped device main unit 14 in which an intraocular lens 12 described later is set. With the description below, the leftward direction in FIG. 1 is the axial forward direction of the intraocular lens insertion device, and the rightward direction in FIG. 1 is the axial backward direction. Also, the vertical direction of FIG. 2 is used as the height direction, and also, the vertical direction in FIG. 1 is used as the width direction.

Figure 3:
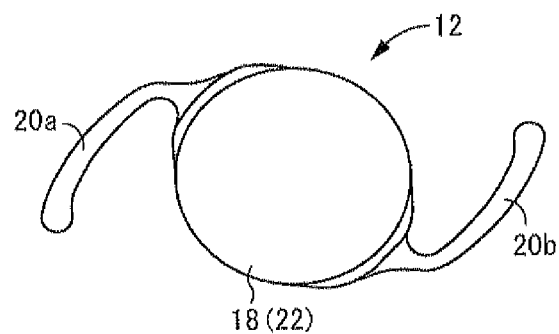
FIG. 3 is a plan view showing an intraocular lens set in a device main unit of the intraocular lens insertion device shown in FIG. 1.
Figure 4:
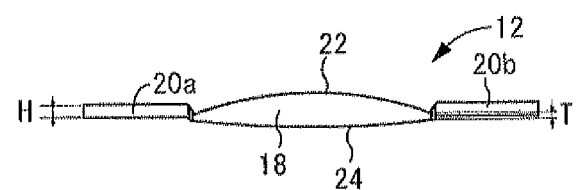
FIG. 4 is a side view of the intraocular lens shown in FIG. 3.

In more detail, the intraocular lens 12 is an intraocular lens 12 that is well known from the past, and as shown in FIG. 3 and FIG. 4, has a one piece constitution in which a pair of haptics 20a, 20b are formed integrally with an optical portion 18. The optical portion 18 gives the optical characteristics, and the item in the drawing which is in a state arranged inside the crystalline lens capsule has optical portion front surface 22 positioned at the cornea side within the capsule and optical portion back surface 24 positioned at the vitreous body side being formed with mutually different curvatures.

The pair of haptics 20a, 20b project from the outer periphery part facing opposite in the radial direction of the optical portion 18, and sandwich the optical portion 18 while facing the outer peripheral side for which they are roughly facing opposite to each other. Also, the projecting tip part of the pair of haptics 20a, 20b extend curving toward the same direction mutual to each other in the peripheral direction of the optical portion 18. With this embodiment the haptic 20a, 20b thickness dimension (optical portion 18 optical axis direction dimension): H is greater than the optical portion 18 outer periphery edge part thickness dimension: T.

The device main unit 14 in which this kind of intraocular lens 12 is set is formed by a hard synthetic resin material having optical transparency, and is equipped with a main unit tube part 28 for which a center hole 26 is formed extending straight in the axial direction with a roughly rectangular cross section shape. A stage 30 is provided further in the axial forward direction than the main unit tube part 28.

On the stage 30, a concave groove 32 extending in the axis direction opening upward is formed in a state communicating with the center hole 26 of the main unit tube part 28. Specifically, the stage 30 is in a state with one long side part removed at the cross section of the main unit tube part 28, and is in a form so as to extend facing the axial direction forward. Then, the bottom surface of the concave groove 32 is used as a lens placement surface 34, and this lens placement surface 34 is a flat surface that broadens in the width direction that is slightly larger than the outer radial direction dimension of the optical portion 18 of the intraocular lens 12. Also, the lens placement surface 34 length dimension (axial direction dimension) is slightly larger than the maximum length dimension containing the haptics 20a, 20b of the intraocular lens 12 (FIG. 3 left and right direction dimension). With this arrangement, at roughly the center part of the lens placement surface 34, the intraocular lens 12 is made to be placed flat in a free state without touching both side walls of the concave groove 32. Also, in this placed-flat state, if an attempt is made to rotate the intraocular lens 12 around the center axis of the optical portion 18, the haptics 20a, 20b touch both side walls of the concave groove 32 and rotation is prevented.

Figure 10:
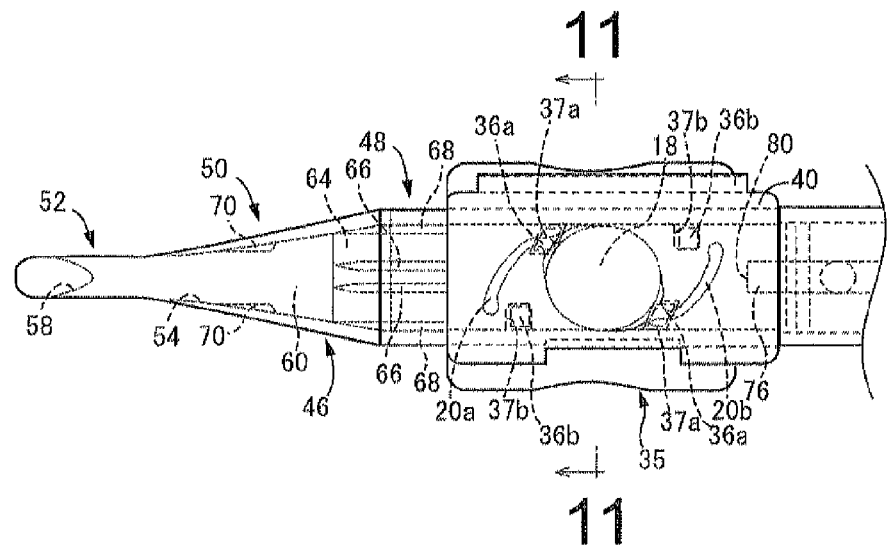
FIG. 10 is an explanatory plan view for explaining a holding state of the intraocular lens in the intraocular lens insertion device shown in FIG. 1.
Figure 11:
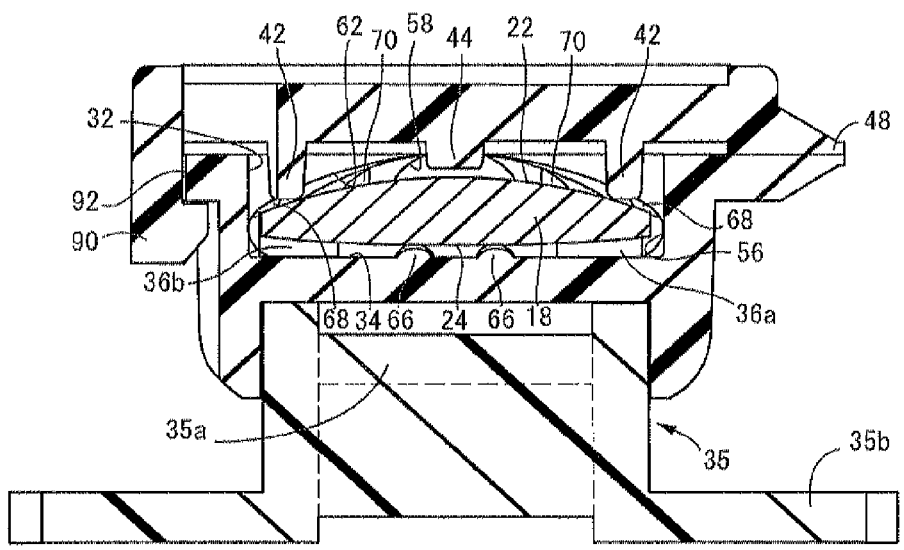
FIG. 11 is an explanatory cross section view correlating to the 11-11 cross section of FIG. 10.

Also, on the stage 30, a support member 35 is attached with the ability to be removed from the outer periphery surface opposite the lens placement surface 34 (see FIGS. 10, 11). The support member 35 is equipped with a base plate part 35a overlapping at the outer surface of the bottom wall part of the concave groove 32 forming the lens placement surface 34, and on this base plate part 35a are formed a plurality of acting projections 36a, 36a, 36b, 36b which project above the overlapping surface to the bottom wall part of the concave groove 32. Also, an operating piece 35b which broadens extending toward the outside opposite to the surface overlapping on the bottom wall part of the concave groove 32 is formed as a single unit on the base plate part 35a.

Then, with the support member 35, its base plate part 35a is attached to the main unit tube part 28 so as to overlap from the outside in relation to the bottom wall part of the concave groove 32 of the stage 30. Also, a plurality of through holes 37a, 37a, 37b, 37b are formed on the bottom wall part of the stage 30 to which the support member 35 is attached. Then, the plurality of acting projections 36a, 36a, 36b, 36b provided projecting on the support member 35 attached to the main unit tube part 28 project to the inner surface of the bottom wall part of the stage 30 through the through holes 37a, 37a, 37b, and 37b.

The number, shape, and forming position of the acting projections 36 are not particularly restricted. Preferably, taking into consideration the shape, size, etc. of the intraocular lens 12 set on the stage 30, setting can be done as appropriate by supporting the intraocular lens 12 held above in a state floating from the bottom wall part of the stage 30, by positioning the intraocular lens 12 within the stage 30, or by preventing displacement of the plunger 16 in the pushing direction in relation to the main unit tube part 28. Then, each position and each shape of the plurality of through holes 37 is set on the stage 30 corresponding to each position and each shape of that plurality of acting projections 36. In particular, with this embodiment, two acting projections 36a, 36a that hold up and support the intraocular lens 12 and two acting projections 36b, 36b that position the intraocular lens 12 are provided.

Also, with the support member 35, it is preferable that a locking mechanism that can be released or the like be provided so as to stably hold it in an attached state on the main unit tube part 28. Specifically, though it is possible to do something like hold the support member 35 in an attached state on the main unit tube part 28 using frictional force between two items with the acting projection 36 press fit in the through hole 37, it is preferable to constitute a locking mechanism for which a claw part is provided on the acting projection 36, for example, that holds the support member 35 in an attached state on the main unit tube part 28 by locking this claw part in the through hole 37 or the like.

Meanwhile, a lid unit 40 connected with the stage 30 by a hinge 38 is provided at one width direction side of the stage 30 (upward side in FIG. 1), and the upper side opening of the concave groove 32 is able to be covered by the lid unit 40. On the lid unit 40, in a state with the upper side opening of the concave groove 32 covered, a pair of left and right guide plate units 42, 42 are provided extending in the axial direction projecting toward the lens placement surface 34. Also, on the lid unit 40, between the pair of left and right guide plate units 42, 42, a center guide plate unit 44 extending in parallel to the left and right guide plate units 42, 42 is provided projecting in the same direction as the left and right guide plate units 42, 42. By doing this, in a state with the lid unit 40 closed, excessive displacement upward of the intraocular lens 12 is restricted, and it is possible to smoothly guide the intraocular lens 12 to the nozzle unit 46 described later.

Figure 5:
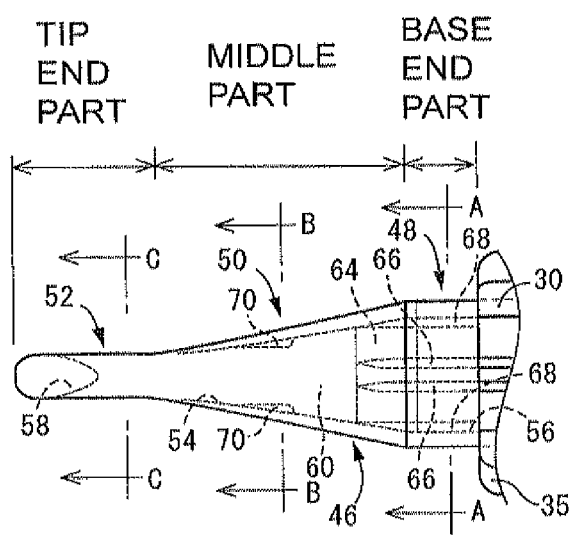
FIG. 5 is an explanatory plan view showing a nozzle unit provided on the device main unit of the intraocular lens insertion device shown in FIG. 1.
Figure 6:
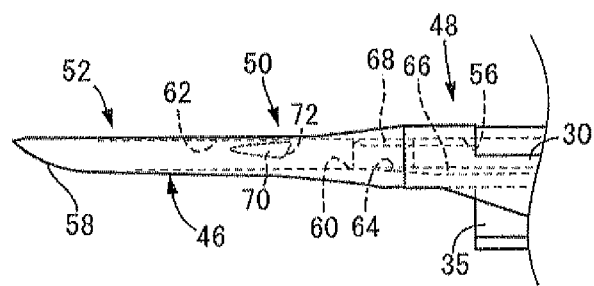
FIG. 6 is an explanatory side view of the nozzle unit shown in FIG. 5.

The nozzle unit 46 is provided further in the axial forward direction than the stage 30 on the device main unit 14. As shown in FIGS. 5 to 7, with the nozzle unit 46, the sequence from the stage 30 side is the base end part 48, the middle part 50, and the tip end part 52, and overall this exhibits an external shape that becomes tapered as it goes from the base side to the tip side. The base end part 48 and the tip end part 52 extend straight in the axial direction in a roughly constant cross section shape. Meanwhile, the middle part 50 is a tapered shaped gradually contracting cross section part for which the cross section shape gradually becomes smaller as it goes in the axial forward direction.

On the nozzle unit 46, a through hole 54 is formed extending along the entire length in the axial direction in a state communicating with the concave groove 32, and the width dimension of the base end side opening part 56 of the through hole 54 is roughly the same size as the groove width dimension of the concave groove 32 (width dimension of the lens placement surface 34). Also, the through hole 54 has a half moon shaped or stacked-rice-cake shaped opening cross section at the base end side opening part 56, but the opening cross section is deformed gradually to a roughly oval shape as it goes to the tip end side opening part 58. By doing this, with the intraocular lens 12 in a non-deformed free state, it is difficult to move the middle part 50, and the optical portion 18 is curved and deformed at the stage when delivering to the middle part 50. As shown in FIG. 7, the through hole 54 of the nozzle unit 46 has a horizontally spreading flat cross section shape for which the vertical direction in FIG. 5 that is the width direction of the stage 30 is the width direction, and the vertical direction in FIG. 6 is the height direction. Also, its flatness ratio (flatness degree) is greater at the base end side opening part 56 than the tip end side opening part 58, and gradually changes at the middle part 50.

Also, formed on the through hole 54 are a bottom surface 60 connected without steps from the lens placement surface 34, and a top surface 62 positioned above the bottom surface 60. On the bottom surface 60, a tilted surface 64 which gradually rises as it goes in the axial forward direction is formed extending across the base end part 48 and the middle part 50. The bottom surface 60 is a flat surface for both side parts of the axial direction sandwiching the tilted surface 64. Meanwhile, the top surface 62 is a flat surface with no steps along the entire length of the axial direction.

A pair of guide rails 66, 66 projecting toward the top surface 62 are formed at the width direction center part of the bottom surface 60 of the base end part 48. The guide rails 66, 66 are projections extending in a straight line in the axial direction across a specified dimension, and their tip parts (axial front side end part) are positioned at the tip of the tilted surface 64 (axial front end). The tip parts of the guide rails 66, 66 are made to be gradually drawn into the bottom surface 60 as they go toward the tip by the tilted surface 64 rising gradually as it goes in the axial forward direction, and have the same height position as the bottom surface 60. Meanwhile, the back end part of the guide rails 66, 66 extend out to the lens placement surface 34 past the back end of the base end part 48. This kind of guide rails 66, 66 are formed roughly parallel to each other separated by a specified distance in the width direction sandwiching the width direction center of the bottom surface 60.

On both end parts of the width direction on the top surface 62 of the base end part 48 are respectively formed side rails 68 projecting toward the bottom surface 60. The side rails 68 project extending in a straight line in the axial direction across a specified dimension, and the tip parts (axial front side tip parts) are in roughly the same axial direction position as the tip parts of the guide rails 66, 66. The tip parts of the side rails 68 are made to be gradually drawn into the inner surface of the nozzle unit 46 as it goes to the tip part (axial forward direction), and are made to be equivalent to the inner surface of the nozzle unit 46. Meanwhile, the back end parts of the side rails 68 are positioned at the base end side opening part 56 which becomes the back end of the base end part 48. This kind of side rails 68 are formed roughly parallel to each other.

At both end parts of the width direction at the top surface 62 of the middle part 50 are respectively formed convex parts 70 as the interfering acting part (engaging part) formed projecting facing the flat bottom surface 60 positioned more to the axial forward direction than the tilted surface 64. Specifically, with this embodiment, the insertion tube part is constituted by the nozzle unit 46 constituted including the middle part 50.

The convex parts 70 are made to project extending in a straight line in the axial direction across a specified dimension, and are formed as a single unit with the middle part 50. The convex parts 70 do not have to be formed as a single unit with the middle part 50, but can also be formed as separate units from the middle part 50 and be attached later using an adhesive agent or the like to the top surface 62 of the middle part 50.

The tip parts of the convex parts 70 (axial front side end parts) are made to be gradually drawn into the top surface 62 of the middle part 50 as it goes to the tip (axial forward direction), and are made to be equivalent to the top surface 62 of the middle part 50. By doing this, the projection height of the convex parts 70 from the top surface 62 is the largest at the axial back side, and gradually gets smaller as it goes from the axial back side to the front.

The convex parts 70 are formed roughly parallel to each other at the position where the height from the bottom surface 60 is roughly the same, and the separation distance in the width direction of the device main unit 14 for these convex parts 70 is roughly fixed across the entire length of the convex part 70. The separation distance in the width direction of the device main unit 14 for the pair of convex parts 70, 70 is bigger than the width dimension of the through hole 54 on the tip end part 52.

On the convex parts 70, formed at the axial back end is the interfering surface 72 that interferes with the haptic 20a facing the front side in the movement direction of the intraocular lens 12 moving inside the nozzle unit 46 as described later. The interfering surface 72 is a tilted surface gradually approaching the bottom surface 60 as it goes in the axial forward direction, and is formed across roughly the entire length in the height direction of the convex part 70.

The convex parts 70 are at a position separated above from the bottom surface 60 of the middle part 50, and a specified gap 74 is formed between the convex parts 70 and the bottom surface 60 of the middle part 50. This gap 74 dimension: S is greater than the outer peripheral edge part thickness dimension: T of the optical portion 18 of the intraocular lens 12.

Figure 8:
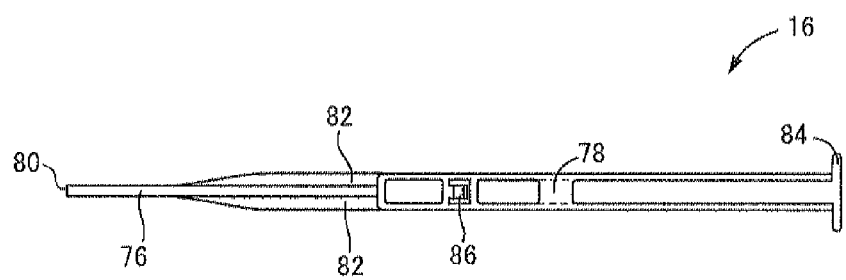
FIG. 8 is a plan view of a plunger constituting the intraocular lens insertion device shown in FIG. 1.
Figure 9:
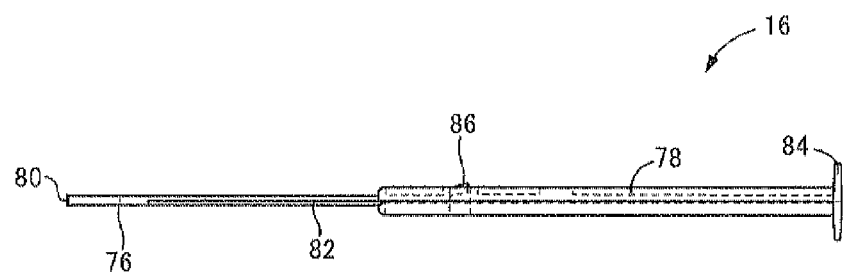
FIG. 9 is a side view of the plunger shown in FIG. 8.

From the axial back side of this kind of device main unit 14, the plunger 16 is inserted into the center hole 26 and attached to the device main unit 14. The plunger 16, as shown in FIG. 8 and FIG. 9, exhibits roughly a rod shape, and is equipped with an acting part 76 positioned at the axial front side and an insertion part 78 positioned further to the axial back side than the acting part 76.

The acting part 76 has a rod shape extending straight in the axial direction having a roughly oval shaped fixed cross section shape, and its tip surface is used as the lens pressing surface 80 that broadens in the axial right angle direction. Thin plate shaped reinforcing ribs 82 are provided at both sides in the width direction of the acting part 76. Meanwhile, the insertion part 78 has a rod shape extending straight with an H shaped cross section overall, and at its back end, formed as a single unit broadening in the axis right angle direction is a pressing plate 84 which adds pushing force when pushing the plunger 16.

This kind of plunger 16 is attached to the device main unit 14 by being inserted in the main unit tube part 28 from the acting part 76 side. By doing this, the intraocular lens insertion device 10 is obtained. When attaching the plunger 16 to the device main unit 14, the initial position of the plunger 16 in relation to the device main unit 14 is set by the engaging claw 86 provided on the insertion part 78 being engaged with the engaging hole 88 formed on the main unit tube part 28. This plunger 16 is prevented from being extracted from the main unit tube part 28 by the engaging action of the engaging claw 86 in the engaging hole 88, and can be displaced using a specified resistance force in the pushing direction to the main unit tube part 28.

Also, the intraocular lens 12 is set in the intraocular lens insertion device 10 for which the plunger 16 is attached at the initial position in relation to the device main unit 14 as described above.

In specific terms, with the device main unit 14, by housing the intraocular lens 12 in the concave groove 32 of the stage 30 opened with the lid unit 40 open, the intraocular lens 12 is arranged in the stage 30. In particular with this embodiment, the intraocular lens 12 is housed in the concave groove 32 with the optical portion back surface 24 on the bottom side, and it is supported and positioned and set by the acting projections 36a, 36a, 36b, 36b of the support member 35 attached to the stage 30. Then, the base end parts of the haptics 20a, 20b of the intraocular lens 12 are placed on the top end surface of the two acting projections 36a, 36a, essentially the entire intraocular lens 12 is brought up from the bottom surface of the concave groove 32, and is set in a state for which action on the optical portion 18 by the contact stress on the bottom surface is avoided as much as possible.

Also, the intraocular lens 12 supported by the two acting projecting parts 36a, 36a is held in a free state with acting stress and distortion reduced on the optical portion 18, and the pair of haptics 20a, 20b extend out toward both sides in the axial direction of the device main unit 14 (front-back direction). Then, the two acting projecting parts 36b, 36b are positioned between the optical portion 18 of the intraocular lens 12 and the haptics 20a, 20b, and by the engaging action of the acting projecting parts 36b, 36b and the optical portion 18 or the haptics 20a, 20b, the intraocular lens 12 is positioned in the axial direction (groove direction of the concave groove 32). Also, the haptic 20b positioned further to the axial back side than the optical portion 18 is positioned slightly separated forward in the extrusion direction from the lens pressing surface 80 of the plunger 16 in its initial position.

After housing the intraocular lens 12 inside the concave groove 32 of the stage 30 in this way, by closing the lid unit 40, the top side opening of the concave groove 32 is covered by the lid unit 40. By doing this, as shown in FIG. 10 and FIG. 11, the intraocular lens 12 is set in a state housed within the device main unit 14. With the lid unit 40 in a closed state, the engaging piece 90 provided on the lid unit 40 is engaged with the engaging notch 92 provided on the stage 30, and the closed state of the lid unit 40 is maintained.

The plunger 16 can also be inserted in the device main unit 14 and set at the initial position before the intraocular lens 12 is housed inside the concave groove 32 of the stage 30, but it is also possible to insert the plunger 16 in the device main unit 14 after the intraocular lens 12 is housed inside the concave groove 32, or furthermore after the lid unit 40 is closed.

After that, the intraocular lens insertion device 10 in which the intraocular lens 12 is set is provided housed and shipped packed in an airtight case or the like. At that time, suitable disinfection or the like is implemented with the processes before or after packing in an airtight case, or with both processes before and after packing.

Incidentally, when inserting the intraocular lens 12 into the eye using the intraocular lens insertion device provided in this way, first, with the intraocular lens insertion device 10 taken out from the packaging at the surgery location, the support member 35 is drawn to under the stage 30, and removed from the device main unit 14. As a result, the intraocular lens 12 is placed directly in a free expanded state on the lens placement surface 34 which is the bottom surface of the stage 30 of the device main unit 14. In other words, the support and positioning of the intraocular lens 12 by the plurality of acting projecting parts 36a, 36a, 36b, 36b formed on the support member 35 are cancelled, and it is possible to move above the lens placement surface 34 of the stage 30. Under these conditions, the center part of the optical portion back surface 24 of the intraocular lens 12 is made to contact and placed on the guide rails 66, 66.

It is also possible to inject a suitable lubricating agent into the interior of the stage 30 or the nozzle unit 46 through an injection hole 94 formed on the lid unit 40. By doing this, as described later, it is possible to more effectively maintain the curved state of the haptic 20a positioned at the movement direction front side by using the viscosity or surface tension or the like of the lubricating agent that exists around the haptic 20a.

When the support member 35 is removed from the device main unit 14, the tip end side opening part 58 of the nozzle unit 46 is inserted in the incision provided in the ocular tissue. Then, while maintaining the insertion state of the nozzle unit 46 in the incision, the plunger 16 is pushed into the device main unit 14. As a result, the lens pressing surface 80 of the plunger 16 contacts the haptic 20b positioned at the axial back side (back side in the movement direction) of the intraocular lens 12, and the intraocular lens 12 is moved toward the nozzle unit 46 while being pressed by the plunger 16.

Figure 12A:
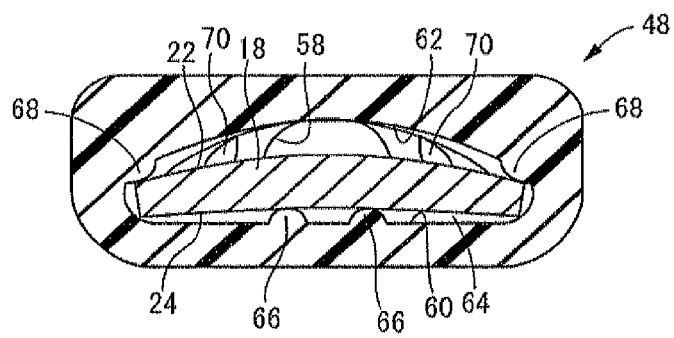
FIGS. 12A-12C are explanatory cross section views for explaining a deformation state of the intraocular lens.

As shown in FIG. 12A, with the intraocular lens 12 delivered to the base end part 48, the center part of the optical portion back surface 24 is in contact with the guide rails 66, 66, and the side rails 68, 68 are in contact with both side end parts in the direction orthogonal to the extrusion direction at the optical portion front surface 22. By doing this, while external force toward the top surface 62 is applied to the center part of the optical portion back surface 24, external force toward the bottom surface 60 is applied to both side end parts in the direction orthogonal to the extrusion direction at the optical portion front surface 22. As a result, with the optical portion 18 of the intraocular lens 12, the optical portion front surface 22 becomes convex facing the top surface 62, and also is deformed to a mountain fold with a ridge line extending in the movement direction of the intraocular lens 12. With FIGS. 12A-12C, the state of the optical portion 18 of the intraocular lens 12 being deformed to a mountain fold is illustrated as a model, and an illustration of the haptics 20a, 20b has been omitted.

Figure 12B:
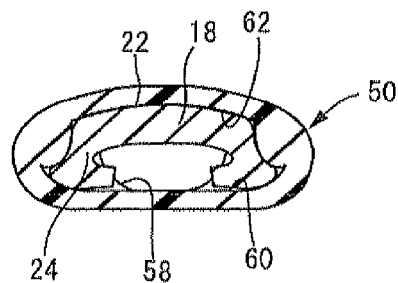
Figure 12C:
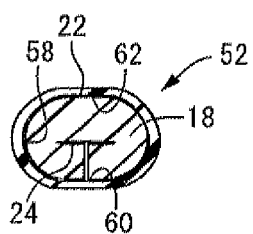

As shown in FIG. 12B, while the intraocular lens 12 for which the initial mountain fold state deformation was applied with the base end part 48 is deformed to be smaller through the middle part 50, it is sent toward the tip end side opening part 58 of the nozzle unit 46. At that time, the optical portion 18 is deformed along the internal surface shape of the through hole 54, the mountain fold state advances even further, and the optical portion 18 is rounded with the optical portion front surface 22 contacting the top surface 62. Then, as shown in FIG. 12C, the optical portion 18 is rounded to be small in a roughly oval shape at the tip end part 52 of the nozzle unit 46 by the through hole 54 which is gradually made into roughly an oval shape as it goes to the tip end part 52.

Specifically, with this embodiment, a deformation guide member is constituted including a pair of guide rails 66, 66, a pair of side rails 68, 68, and a specially shaped through hole 54 formed on the nozzle unit 46.

The deformation guide member is not limited to being an item constituted by each pair of guide rails 66, 66, side rails 68, 68, and through hole 54 shown with this embodiment. For example, even with a through hole 54 that is not equipped with guide rails 66 and side rails 68, it is also possible to constitute the deformation guide member by appropriately setting the change state of its cross section shape and extrusion direction or the like and doing folding deformation of the intraocular lens 12 to a mountain shape, and also possible to constitute a deformation guide member by forming partial convex parts and concave parts inside the through hole 54.

Figure 14:
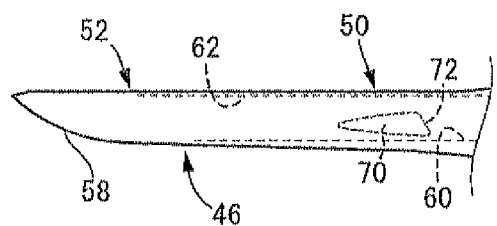
FIG. 14 is a side view for explaining another mode of the deformation guide member that can be applied with the present invention.

It is also possible for the deformation guide member to not be an item for which the optical portion 18 is deformed to a mountain fold shape as described above, but rather to be an item for which the optical portion 18 is deformed to be a valley fold shape whereby the optical portion back surface 24 is made to be convex facing the bottom surface 60 and the valley line extends in the movement direction of the intraocular lens 12. As the deformation guide member for realizing the valley fold state, for example as shown in FIG. 13, it is possible to use a through hole with a cross section shape for which the through hole 54 of the embodiment noted above is inverted in terms of top and bottom, or the like. Also, with this deformation guide member, as shown in FIG. 14, it is preferable that the interfering surface 72 of the convex part 70 be a tilted surface that gradually approaches the top surface 62 side as it goes to the axial forward direction.

Figure 15:
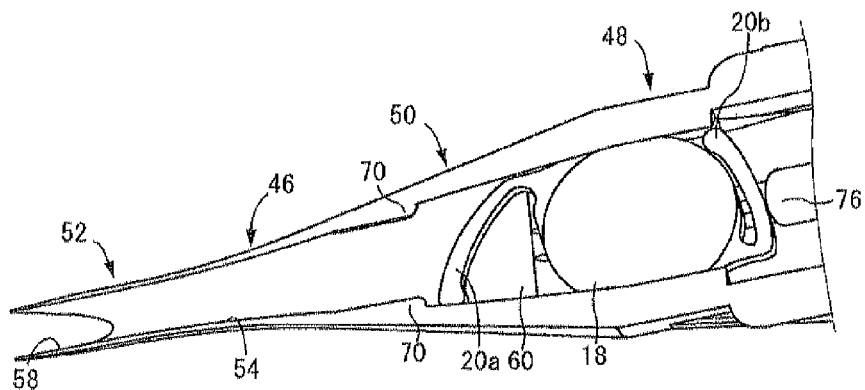
FIG. 15 is a perspective view for explaining a contact state of a haptic positioned at the movement direction front side to a convex part.
Figure 16:
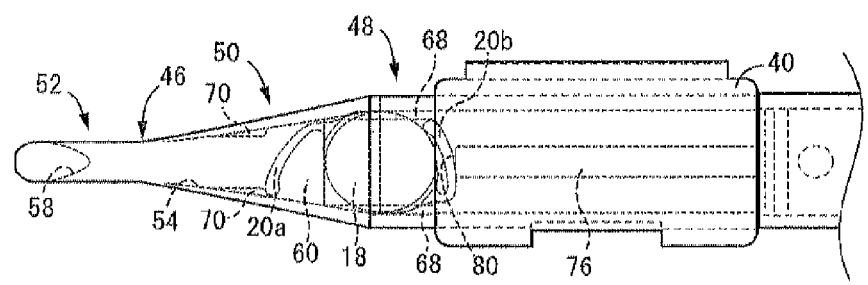
FIG. 16 is a plan view for explaining the contact state of the haptic positioned at the movement direction front side to the convex part.
Figure 17:
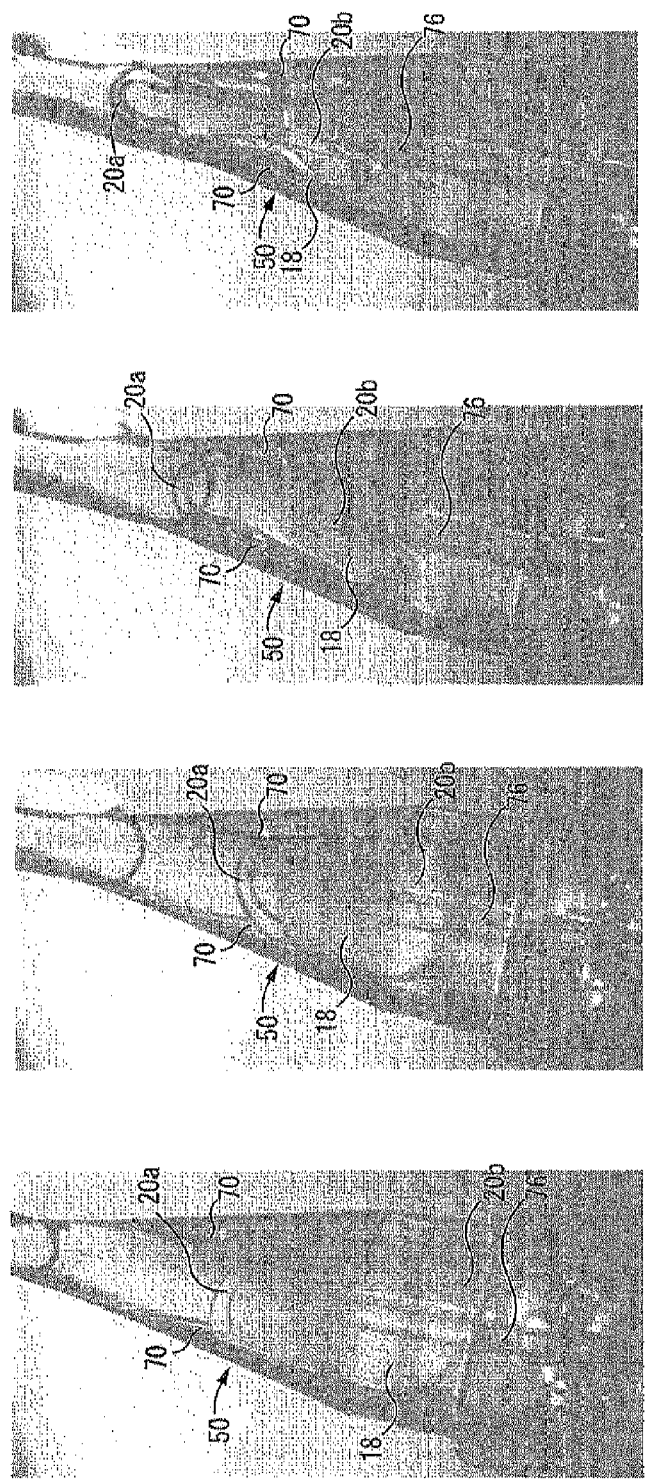
FIGS. 17A-17D are photographs for explaining the contact state of the haptic positioned at the movement direction front side to the convex part.
Figure 18:
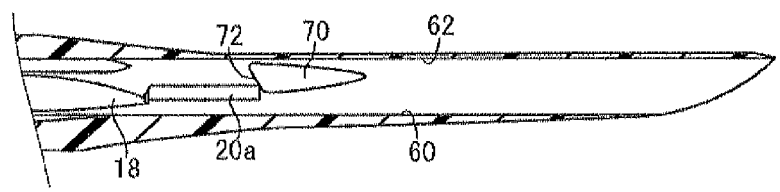
FIG. 18 is an explanatory cross section view for explaining the contact state of the haptic positioned at the movement direction front side to the convex part.

And as shown in FIG. 15, FIG. 16, and also FIG. 17A, with the intraocular lens 12 delivered to the base end part 48, the tip part of the haptic 20a positioned at the axial front side (movement direction front side) is in contact with the convex part 70 of the width direction other side. At that time, as shown in FIG. 18, the tip part of the haptic 20a is in contact with the interfering surface 72 formed on the convex part 70. By doing this, an external force is applied toward the movement direction back side on the haptic 20a, and the haptic 20a is curved and deformed in the direction approaching the optical portion 18. When doing that, the tip part of the haptic 20a slides toward the bottom surface 60 over the interfering surface 72 along with the movement of the intraocular lens 12 to the tip end side opening part 58. As a result, the tip part of the haptic 20a moves to the concave side of the optical portion 18.

Figure 19:
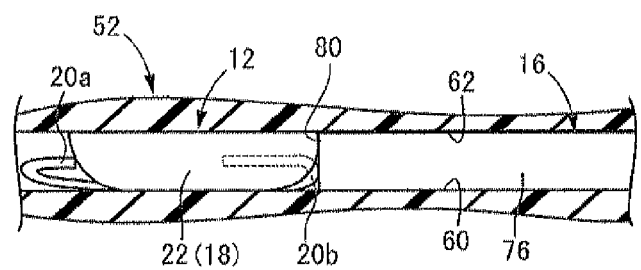
FIG. 19 is an explanatory cross section view for explaining a contact state on an outer periphery edge part of an optical portion by a tip part of the haptic positioned at the movement direction front side.

When the intraocular lens 12 is pushed in further from the state when the tip part of the haptic 20a positioned in the movement direction front side starts being in contact with the convex part 70, as shown in FIG. 17B and FIG. 19, the tip part of the haptic 20a is in contact with the outer peripheral edge part of the optical portion 18. At that time, the base end part of the haptic 20a is in contact with the other convex part 70. The haptic 20b of the movement direction back side starts to slide into the bottom side (concave side) of the optical portion 18 deformed to a mountain fold state.

When the intraocular lens 12 is further pushed in from this state, as shown in FIG. 17C, the haptic 20a of the movement direction front side for which the tip part is in contact with the outer peripheral edge part of the optical portion 18 is curved so as to be convex facing the tip end side opening part 58. At that time, as shown in FIG. 12B, the outer peripheral edge part of the optical portion 18 deformed to a mountain fold state is made to pass through the gap 74 formed between the convex part 70 and the bottom surface 60. The haptic 20b of the movement direction back side slides into the concave side of the optical portion 18 deformed to a mountain fold state, and extends toward the tip end side opening part 58.

Then, as shown in FIG. 17D, in a state with the haptic 20a curved and deformed to the point that the tip part of the haptic 20a positioned at the movement direction front side is in contact with the outer peripheral edge parts of the optical portion 18, the intraocular lens 12 is moved up to the tip end side opening part 58 within the nozzle unit 46.

The curve deformation of the haptic 20a is not limited to a state of the tip part being in contact with the outer peripheral edge part of the optical portion 18 as shown in the drawing. For example, it is also possible to have the deformation volume suppressed to the level that the tip part of the haptic 20a is not in contact with the optical portion 18, and conversely, it is also possible to have a deformation volume big enough for the haptic 20a to enter inside the concave side of the optical portion 18 which has been deformed to a mountain fold state. By having the curve deformation be big enough that the haptic 20a enters inside the concave side of the optical portion 18 which is deformed to a mountain fold state so that it is in a locked tucking state, it is possible to further delay the extension to the front of the haptic 20a with the intraocular lens 12 inserted in the capsule. Specifically, the level of curve deformation of the haptic 20a can be set as appropriate according to the haptic 20a properties or the characteristics of the used lubricating agent or the like according to the material of the intraocular lens 12 or the like.

With the intraocular lens 12 extruded from the tip end side opening part 58 of the nozzle unit 46, the optical portion 18 is expanded and deformed within the capsule. At that time, the haptic 20a positioned at the movement direction front side of the intraocular lens 12 is also expanded and deformed. By doing this, pressing of the haptic 20a on the intracapsular surface ahead of the optical portion 18 expansion deformation is avoided, and expansion deformation that is accompanied by rotation of the optical portion 18 with the pressing point of the haptic 20a on the intracapsular surface as the center is prevented. As a result, the undesirable inversion of the optical portion 18 by the practitioner when inserting the intraocular lens 12 into the eye is effectively prevented.

Therefore, if using the intraocular lens insertion device 10 as described above, it is possible to more reliably arrange the front-back surfaces 22, 24 of the intraocular lens 12 in the proper direction.

Figure 20:
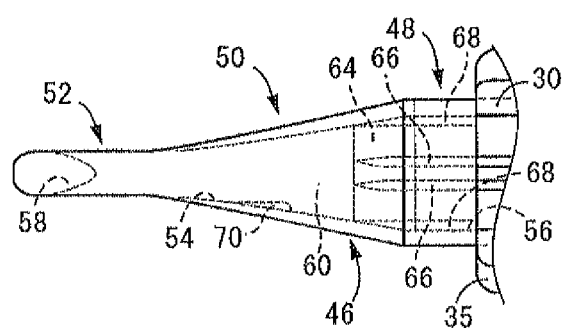
FIG. 20 is an explanatory plan view for explaining a mode for which the convex part is provided only at the other end part of the width direction of the middle part which can be used for the present invention.

Also, since the convex parts 70 are provided at both side end parts in the width direction of the middle part 50, when the front and back of the intraocular lens 12 is inverted (the optical portion front surface 22 side faces downward) and it is set on the lens placement surface 34, the tip part of the haptic 20a is engaged with the other convex part 70 (convex part 70 positioned in the upper side in FIG. 1). Specifically, as described earlier, even if the optical portion 18 has the front and back inverted and is set on the lens placement surface 34, it is possible to obtain effective exhibition of the interfering action of the convex part 70 in relation to the haptic 20a. Of course this convex part 70 does not need to be provided at both side end parts in the width direction of the middle part 50. For example, in a case such as when the front and back of the intraocular lens 12 set on the lens placement surface 34 is specified and the extending direction of the haptic 20a is predetermined, it is also possible to provide it only at one end side of the width direction of the middle part 50 as shown in FIG. 20.

Also, the gap 74 is formed between the convex part 70 and the bottom surface 60, and the intraocular lens 12 is made to move forward while the outer peripheral edge part of the optical portion 18 that is deformed to a mountain fold state is allowed to enter this gap 74. Because of that, when the intraocular lens 12 is moved inside the nozzle unit 46, there is a reduction or avoidance of the occurrence of problems such as the outer peripheral edge part of the optical portion 18 catching on the convex part 70, and it is possible to reduce the movement resistance force of the intraocular lens 12.

In particular, with a one piece constitution intraocular lens 12, typically, to ensure strength and the like of the haptics 20a, 20b formed with a soft material the same as the optical portion 18, the haptics 20a, 20b are thicker in the optical axis direction of the optical portion 18 than the outer peripheral edge part of the optical portion 18. Because of that, when moving the intraocular lens 12, while the haptic 20a easily catches on the convex part 70 and curves to the optical portion 18 side even when there is a gap 74, because of the existence of the gap 74, the outer peripheral edge part of the optical portion 18 easily passes through the part at which the convex part 70 is formed by entering into the gap 74.

Furthermore, with the intraocular lens insertion device 10 of this embodiment, the intraocular lens 12 is set in a free state for which deformation due to external force is not applied, and in a state placed flat, and with the movement midway inside the nozzle unit 46 that comes with extrusion by the plunger 16 for inserting into the eye, curve deformation is applied to the haptic 20a. Because of that, it is possible to make the holding time of the deformation state for the optical portion 18 or the haptic 20a shorter, and to suppress to the extent possible the stress and deformation that remains on the optical portion 18 or the haptic 20a. Also, special work processes for deforming the optical portion 18 to be smaller or curving the haptic 20a are not necessary, which makes the burden of the practitioner's work efforts smaller.

Figure 21:
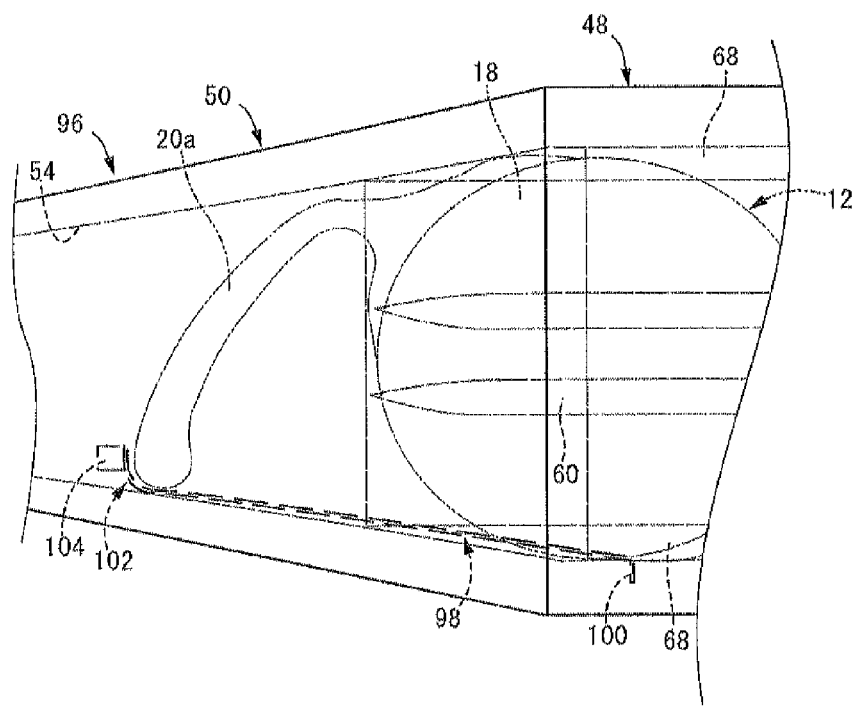
FIG. 21 is an explanatory plan view showing the major parts of an intraocular lens insertion device as a second embodiment of the present invention.
Figure 22:
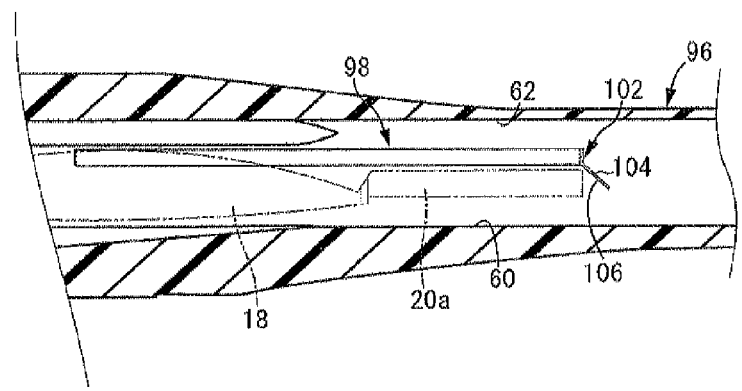
FIG. 22 is an explanatory cross section view showing the major parts of the intraocular lens insertion device shown in FIG. 21.

Next, we will describe the intraocular lens insertion device 96 as a second embodiment of the present invention while referring to FIG. 21 and FIG. 22. With the second embodiment noted hereafter and the third to eighth embodiments described later, members and parts having the same constitution as the first embodiment are given the same code number as those of the first embodiment in the drawings, and a detailed explanation of those will be omitted.

The intraocular lens insertion device 96 of this embodiment is provided with a flexible locking piece 98 as the interfering acting part (engaging part) instead of the convex part (70) with the intraocular lens insertion device (10) of the first embodiment.

The flexible locking piece 98 is formed from an elastically deformable material such as a synthetic resin material, a rubber material or the like, and overall exhibits a band plate shape. On the flexible locking piece 98, at one end in the lengthwise direction, an attachment piece 100 projecting to one side in the thickness direction is provided, and also, at the other end in the lengthwise direction, an engaging piece 102 projecting to the other side in the thickness direction is provided. The engaging piece 102, extends to one side of the plate width direction of the flexible locking piece 98 at its projecting end side, and the interfering part 104 is constituted by this extending part.

This kind of flexible locking piece 98 is provided extending inside the nozzle unit 46 from the base end side to the tip side by embedding the attachment piece 100 in the other end part of the width direction of the top surface 62 of the base end part 48. By doing this, the engaging piece 102 projects to one side of the width direction from the other end part of the width direction of the top surface 62 of the middle part 50. Also, the engaging piece 102 is placed above the bottom surface 60 at the other side of the width direction, and the interfering part 104 provided at its projecting end extends toward the bottom surface 60. The extending dimension of the interfering part 104 is of a size that does not reach the bottom surface 60. By doing this, a specified gap 74 is formed between the interfering part 104 and the bottom surface 60. Also, an interfering surface 106 given a tilt approaching the bottom surface 60 side as it goes to the axial forward direction is formed on the axial back side of the interfering part 104.

The haptic 20a of the movement direction front side of the intraocular lens 12 moving within the nozzle unit 46 is made to contact this kind of interfering part 104. Then, the haptic 20a in contact with the interfering part 104 is curved and deformed to the direction approaching the optical portion 18 by an external force being applied toward the movement direction back side of the intraocular lens 12 from the interfering part 104. When doing that, the haptic 20a slides over the interfering surface 106 to the bottom surface 60 side.

Also, when the optical portion 18 contacts the interfering part 104, the engaging piece 102 is pressed in the axial forward direction and deformed so as to fall over. By doing this, the projection height of the engaging piece 102 from the top surface 62 becomes smaller. As a result, it is possible to effectively avoid catching of the optical portion 18 by providing the engaging piece 102. As is clear from this, with this embodiment, the insertion tube part is constituted by the nozzle unit 46.

Figure 23:
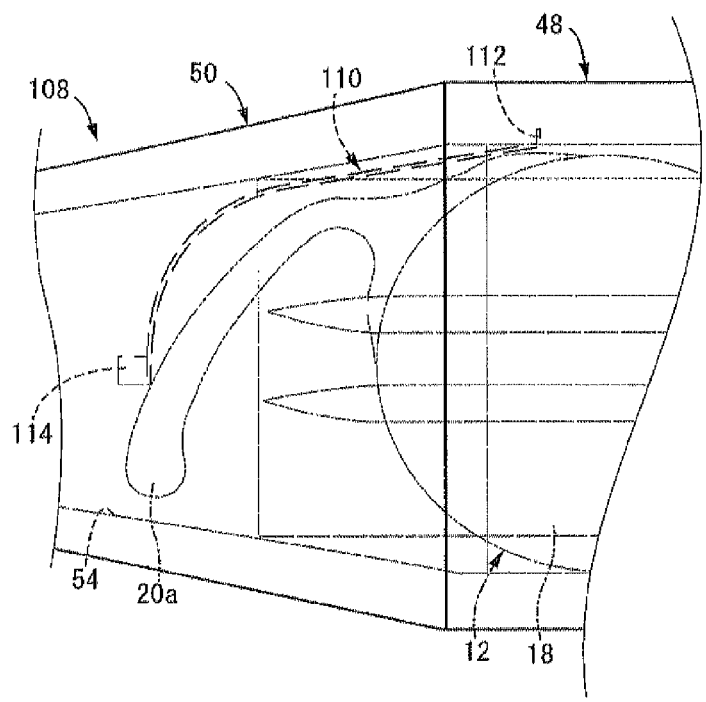
FIG. 23 is an explanatory plan view showing the major parts of an intraocular lens insertion device as a third embodiment of the present invention.
Figure 24:
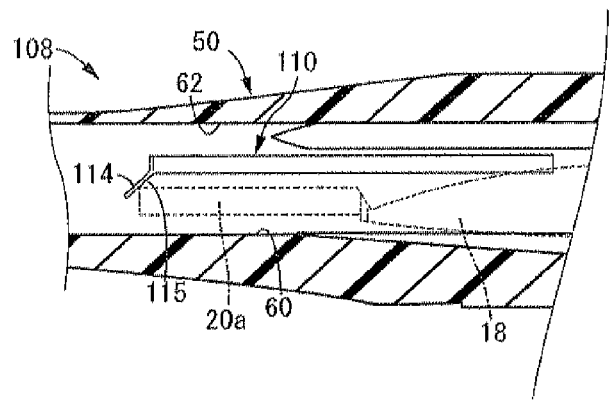
FIG. 24 is an explanatory cross section showing the major parts of the intraocular lens insertion device shown in FIG. 23.

Next, we will describe the intraocular lens insertion device 108 as a third embodiment of the present invention while referring to FIG. 23 and FIG. 24. The intraocular lens insertion device 108 of this embodiment is provided with a flexible locking piece 110 as the interfering acting part (engaging part) instead of the convex part (70) as compared with the intraocular lens insertion device (10) of the first embodiment.

The flexible locking piece 110 is formed with an elastically deformable material such as a synthetic resin material, rubber material or the like, and overall this exhibits a band plate shape. An attachment piece 112 projecting to one side in the thickness direction is provided at the lengthwise direction one end part on the flexible locking piece 110. Also, the flexible locking piece 110 is curved to the other side in the thickness direction across the other end part from the lengthwise direction middle part. Also, an engaging piece 114 projecting to one plate width direction is provided at the lengthwise direction other end part of the flexible locking piece 110.

This kind of flexible locking piece 110 is provided extending into the nozzle unit 46 from the base end side to the tip end side by embedding the attachment piece 112 in the one end part of the width direction of the top surface 62 of the base end part 48. The engaging piece 114 is provided at the tip of the other end part of the lengthwise direction of the flexible locking piece 110 extending while curved to the other side from one side of the width direction of the middle part 50, and with the flexible locking piece 110 provided in a state as described above, is positioned roughly at the center of the width direction of the through hole 54. Also, the engaging piece 114 is positioned above the bottom surface 60, and a specified gap 74 is formed between the engaging piece 114 and the bottom surface 60. Also, an interfering surface 115 which is given a tilt approaching the bottom surface 60 as it goes to the axial forward direction is formed on the axial back side of the engaging piece 114.

The haptic 20a of the movement direction front side of the intraocular lens 12 moving within the nozzle unit 46 is made to be in contact with this kind of engaging piece 114. By doing this, an external force is applied toward the movement direction back side on the haptic 20a, and the haptic 20a is curved and deformed in the direction approaching the optical portion 18. At that time, the haptic 20a slides over the interfering surface 115 to the bottom surface 60 side. As is clear from this, with this embodiment, the insertion tube part is constituted by the nozzle unit 46.

Also, when the optical portion 18 contacts the engaging piece 114, the engaging piece 114 is pressed by the optical portion 18 and moves to one side of the width direction of the middle part 50. Because of that, even if the engaging piece 114 is positioned at the width direction center of the middle part 50, there is no hindering of the passage of the optical portion 18.

Figure 25:
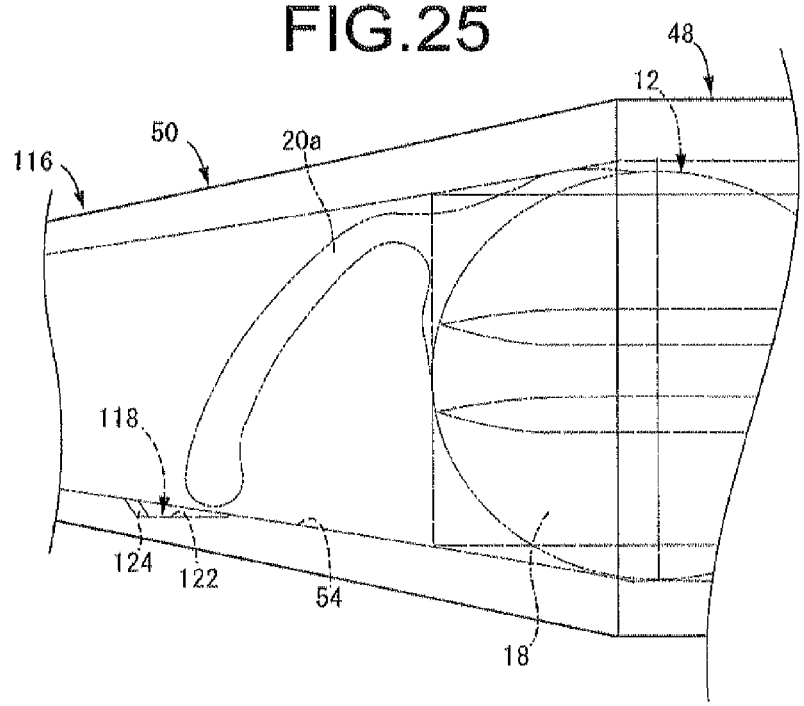
FIG. 25 is an explanatory plan view showing the major parts of an intraocular lens insertion device as a fourth embodiment of the present invention.
Figure 26:
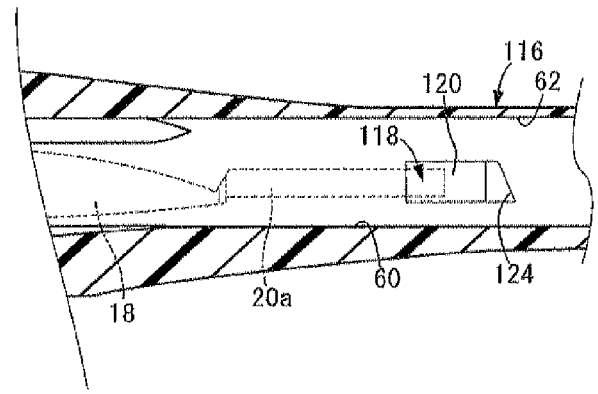
FIG. 26 is an explanatory cross section showing the major parts of the intraocular lens insertion device shown in FIG. 25.

Next, we will describe the intraocular lens insertion device 116 as a fourth embodiment of the present invention based on FIG. 25 and FIG. 26. The intraocular lens insertion device 116 of this embodiment is provided with a concave part 118 as the interfering acting part (engaging part) instead of the convex part (70) as compared with the intraocular lens insertion device (10) of the first embodiment.

The concave part 118 is formed opened at the top surface 62 at the width direction other end part of the top surface 62 of the middle part 50, and is positioned higher than the bottom surface 60. The concave part 118 is equipped with a guide surface 120 extending in the axial direction and an interfering surface 124 positioned further to the axial front side than the guide surface 120 and extending in the tilting direction in relation to the axial direction. A tilt is given to the interfering surface 124 approaching the bottom surface 60 as it goes to the axial forward direction. The concave part 118 can also be formed at both end parts of the width direction of the top surface 62 of the middle part 50.

The haptic 20a of the movement direction front side of the intraocular lens 12 moving within the nozzle unit 46 is entered into this kind of concave part 118. Then, when the haptic 20a contacts the interfering surface 124, an external force is applied on the haptic 20a toward the movement direction back side, and the haptic 20a is curved and deformed in the direction approaching the optical portion 18. At that time, the haptic 20a slides over the interfering surface 124 to the bottom surface 60 side. With this embodiment, the insertion tube part is constituted by the nozzle unit 46. Also, it is acceptable for the haptic 20a to either slide over the guide surface 120 or not slide when it is entered into the concave part 118.

With this kind of intraocular lens insertion device 116, the interfering surface 124 that contacts the haptic 20a on the movement direction front side is formed inside the concave part 118 that opens at the top surface 62 of the middle part 50. Because of that, it is possible to avoid contact by the optical portion 18 on the interfering surface 124.

Figure 27:
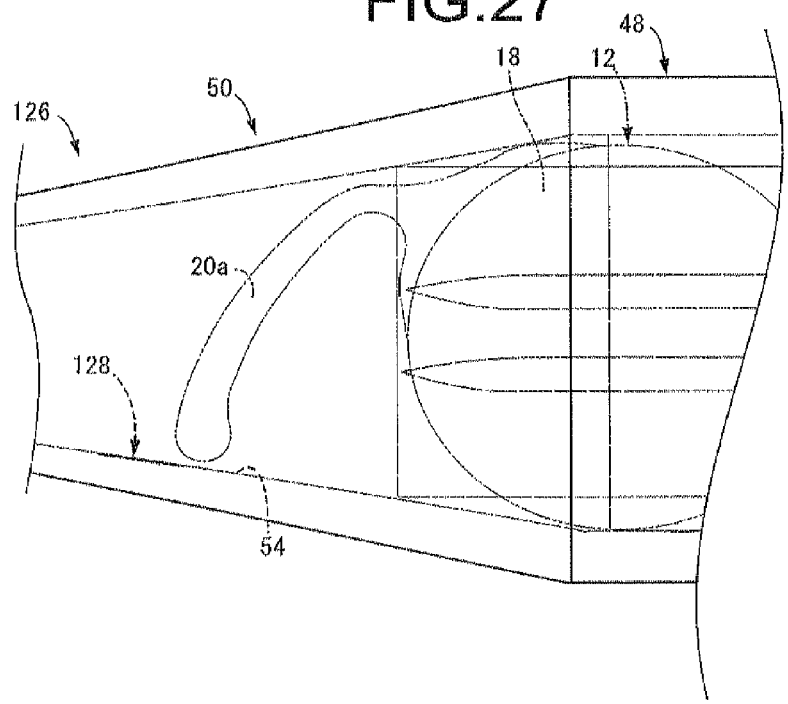
FIG. 27 is an explanatory plan view showing the major parts of an intraocular lens insertion device as a fifth embodiment of the present invention.
Figure 28:
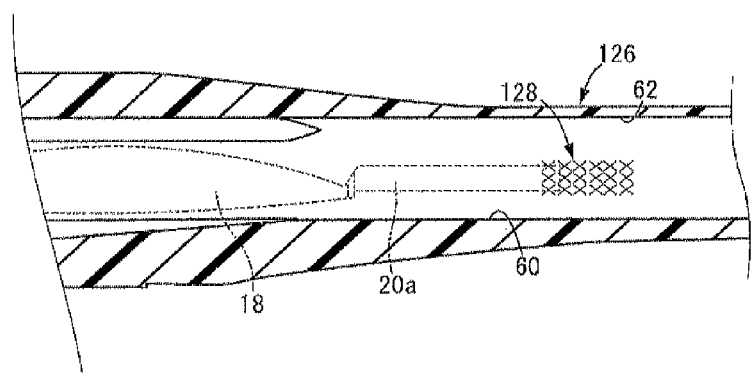
FIG. 28 is an explanatory cross section view showing the major parts of the intraocular lens insertion device shown in FIG. 27.

Next, we will describe the intraocular lens insertion device 126 as a fifth embodiment of the present invention based on FIG. 27 and FIG. 28. The intraocular lens insertion device 126 of this embodiment is provided with a rough surface part 128 as the interfering acting part instead of the convex part (70) as compared with the intraocular lens insertion device (10) of the first embodiment.

The rough surface part 128 is formed on the width direction other end part of the top surface 62 of the middle part 50. The rough surface part 128 is a rougher surface than the part for which the optical portion 18 contacts the top surface 62 (the width direction center part of the top surface 62, for example). By doing this, the rough surface part 128 has greater contact resistance than the part for which the optical portion 18 contacts at the top surface 62. Also, since the rough surface part 128 is provided at the top surface 62 of the middle part 50 midway as the cross section shape of the through hole 54 changes, a tilt is given to the rough surface part 128 approaching the bottom surface 60 as it goes to the axial forward direction.

The haptic 20a of the movement direction front side of the intraocular lens 12 moving within the nozzle unit 46 is made to contact this kind of rough surface part 128. Then, the haptic 20a is displaced approaching the optical portion 18 side by the frictional force between the haptic 20a and the rough surface part 128. At that time, the haptic 20a slides over the rough surface part 128 to the bottom surface 60 side. As is clear from this, with this embodiment, the insertion tube part is constituted by the nozzle unit 46 for which the rough surface part 128 is provided.

With this kind of intraocular lens insertion device 126, using the difference in contact resistance of the contact part of the optical portion 18 with the rough surface part 128 and the top surface 62, the haptic 20a of the movement direction front side is made to approach the optical portion 18 side. Because of that, there is no projection or the like that projects greatly inside the through hole 54 and contacts the optical portion 18. As a result, it is possible to avoid catching on the projection or the like of the optical portion 18.

Figure 29:
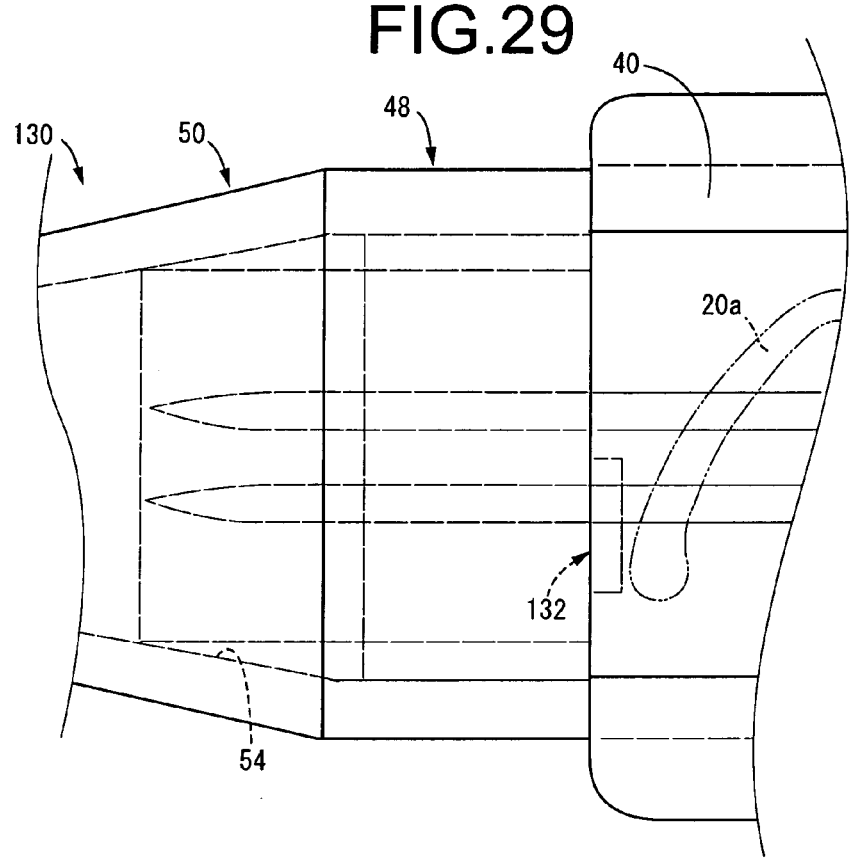
FIG. 29 is an explanatory plan view showing the major parts of an intraocular lens insertion device as a sixth embodiment of the present invention.
Figure 30:
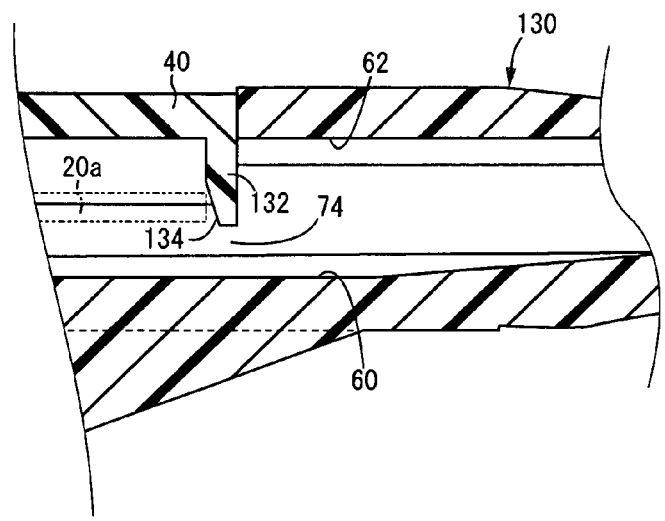
FIG. 30 is an explanatory cross section view showing the major part of the intraocular lens insertion device shown in FIG. 29.

Next, we will describe the intraocular lens insertion device 130 as a sixth embodiment of the present invention based on FIG. 29 and FIG. 30. The intraocular lens insertion device 130 of this embodiment is provided with a flexible projection 132 as the interfering acting part instead of the convex part (70) as compared with the intraocular lens insertion device (10) of the first embodiment.

The flexible projection 132 is formed from a synthetic resin material, rubber material or the like, and overall exhibits a flat plate shape. Also, the flexible projection 132 is provided on the axial front end edge part of the lid unit 40, and in a state with the lid unit 40 closed, is projecting toward the lens placement surface 34. The projection height of the flexible projection 132 is of a size of a level that does not reach the lens placement surface 34 in a state with the lid unit 40 closed. By doing this, in a state with the lid unit 40 closed, the specified gap 74 is formed between the projection end of the flexible projection 132 and the lens placement surface 34. The flexible projection 132 can be formed as a single unit with the lid unit 40, or can be an item formed separately from the lid unit 40 and adhered later using an adhesive agent or the like. At the axial direction back end of the flexible projection 132 is provided an interfering surface 134 given a tilt approaching the bottom surface 60 as it goes to the axial forward direction in a state with the lid unit 40 closed.

The haptic 20a of the movement direction front side of the intraocular lens 12 moving within the nozzle unit 46 is made to be in contact with the interfering surface 134 of this kind of flexible projection 132. By doing this, external force is applied toward the movement direction back side on the haptic 20a, and the haptic 20a is curved and deformed in the direction approaching the optical portion 18. At that time, the haptic 20a slides over the interfering surface 134 to the bottom surface 60 side. Also, when the haptic 20a slides over the interfering surface 134, the flexible projection 132 is curved and deformed to the movement direction front side by its own elasticity. Also, in a state with the flexible projection 132 curved and deformed to the movement direction front side, the intraocular lens 12 moves within the nozzle unit 46. The flexible projection 132 can also be bent in a state in contact with the haptic 20a on the movement direction front side and not return to its original shape. Also, if a suitable lubricating agent is placed in the nozzle unit 46, even if there is no contact with the flexible projection 132, using the interfering action of the lubricating agent, the haptic 20a on the movement direction front side can easily maintain a state approaching the optical portion 18. As is clear from the description above, with this embodiment, the insertion tube part is constituted not only by the nozzle unit 46 but also by a part positioned further to the front than the intraocular lens 12 placed on the lens placement surface 34 at the device main unit 14 (axial front side end part of the stage 30 and the lid unit 40).

Figure 31:
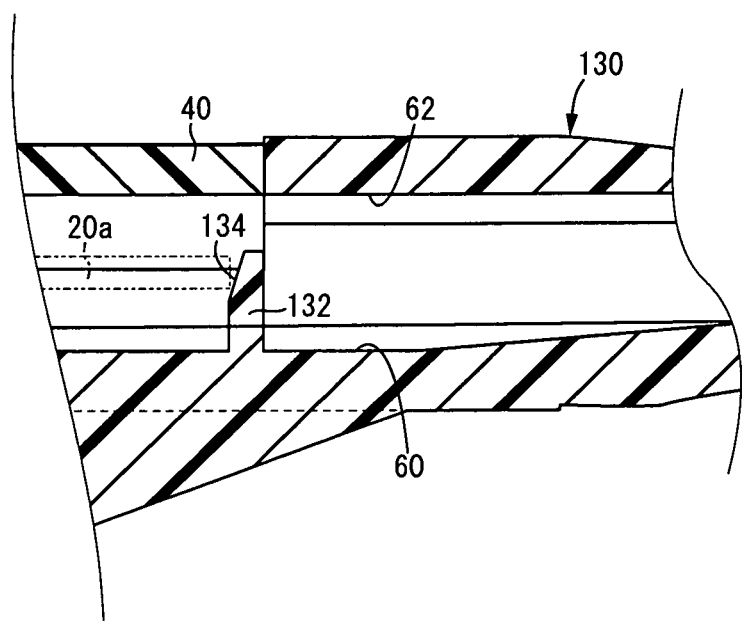
FIG. 31 is an explanatory cross section view for explaining another mode of the flexible projection that can be used with the present invention.

The flexible projection 132 can also project facing upward. For example, as shown in FIG. 31, it is possible to use a flexible projection 132 formed projecting upward from the lens placement surface 34. In this case, by adhering and fixing a flexible projection 132 that was formed separately from the device main unit 14 to the lens placement surface 34, it is possible to provide the flexible projection 132 projecting from the lens placement surface 34. Also, the flexible projection 132 does not have to be provided projecting from the lens placement surface 34, but rather, for example, can be provided projecting from the bottom surface 60 of the base end part 48. Note that to make this easier to understand, the same code number as this embodiment is given to the flexible projection 132 shown in FIG. 31.

Figure 32:
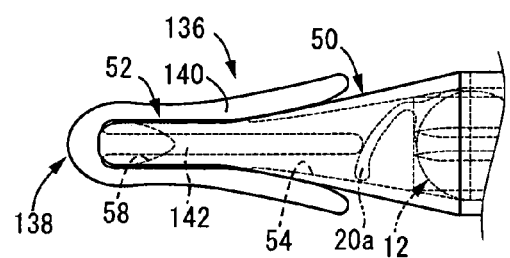
FIG. 32 is an explanatory plan view showing the major parts of an intraocular lens insertion device as a seventh embodiment of the present invention.
Figure 33:
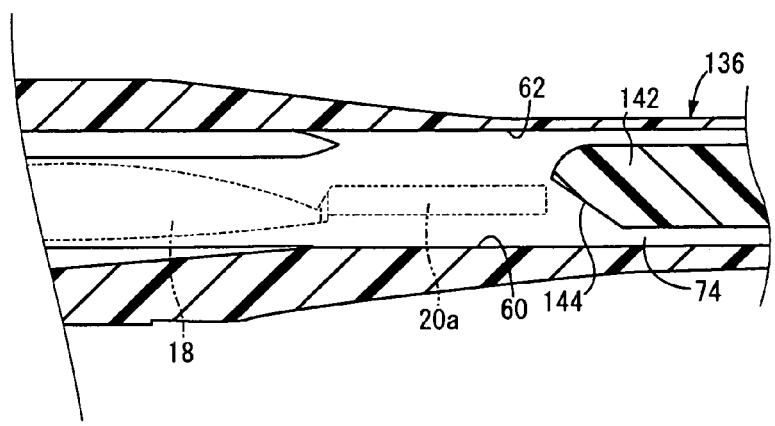
FIG. 33 is an enlarged explanatory cross section showing the major parts of the intraocular lens insertion device shown in FIG. 32.

Next, we will describe the intraocular lens insertion device 136 as a seventh embodiment of the present invention based on FIG. 32 and FIG. 33. To the intraocular lens insertion device 136 of this embodiment, attached is an entry contact member 138 as the interfering acting part instead of the convex part (70) being provided, as compared with the intraocular lens insertion device (10) of the first embodiment.

The entry contact member 138 is formed by a synthetic resin material, rubber material or the like, and is equipped with a sandwiching part 140 that is curved in a U shape or V shape. The sandwiching part 140 can also be a cap form that covers the nozzle unit 46. Also, an entry axis part 142 is provided projecting toward the opening side of the sandwiching part 140 in the valley bottom part of the sandwiching part 140.

This kind of entry contact member 138 is mounted on the nozzle unit 46 by the sandwiching part 140 sandwiching the nozzle unit 46 in the width direction in a state with the entry axis part 142 inserted in the through hole 54 from the tip end side opening part 58 of the nozzle unit 46. In this state, the entry axis part 142 positioned within the through hole 54 is positioned further upward than the bottom surface 60 at the width direction center part of the through hole 54. By doing this, the specified gap 74 is formed between the bottom surface 60 and the entry axis part 142. Also, at the tip of the entry axis part 142 is formed an interfering surface 144 to which is given a tilt gradually approaching the bottom surface 60 as it goes to the axial forward direction of the nozzle unit 46 (base end side of the entry axis part 142), The haptic 20a of the movement direction front side of the intraocular lens 12 moving within the nozzle unit 46 is made to contact the interfering surface 144 of this kind of entry axis part 142. By doing this, external force is applied toward the movement direction back side on the haptic 20a, and the haptic 20a is curved and deformed in the direction approaching the optical portion 18. Then, after the haptic 20a is displaced approaching the optical portion 18 side by the interfering surface 144 of the entry axis part 142, the entry contact member 138 is removed from the nozzle unit 46. After that, the intraocular lens 12 is extruded from the nozzle unit 46 in a state with the haptic 20a approaching the optical portion 18 side. As is clear from this, with this embodiment, the insertion tube part is constituted by the nozzle unit 46 for which the entry contact member 138 is attached. Note that if a suitable lubricating agent is placed inside the nozzle unit 46, even after the entry contact member 138 is removed from the nozzle unit 46, it becomes easier to maintain the state with the haptic 20a approaching the optical portion 18 by the interfering effect of the lubricating agent.

With this kind of intraocular lens insertion device 136, it is not necessary to provide the interfering acting part on the nozzle unit 46, so the manufacturing of the intraocular lens insertion device 136 itself becomes easier.

Figure 34:
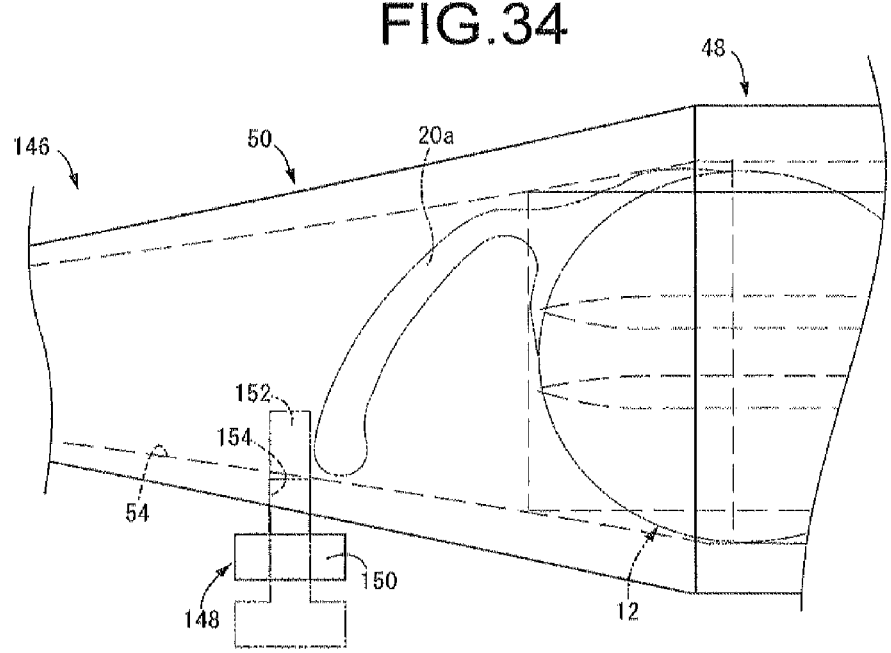
FIG. 34 is an explanatory plan view showing the major parts of an intraocular lens insertion device as an eighth embodiment of the present invention.
Figure 35:
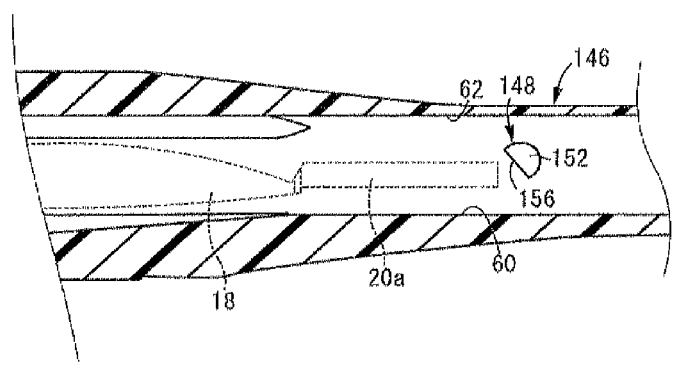
FIG. 35 is an enlarged explanatory cross section view showing the major parts of the intraocular lens insertion device shown in FIG. 34.
Figure 12A:
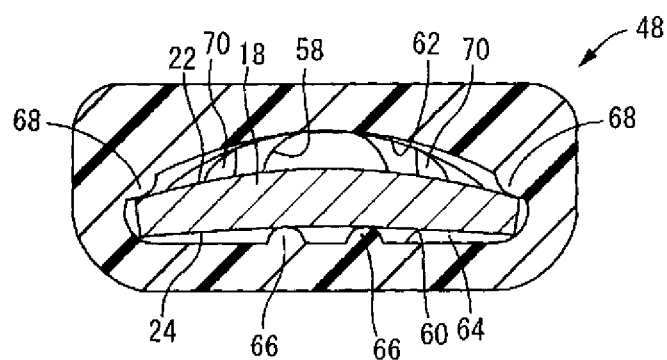
Figure 12B:
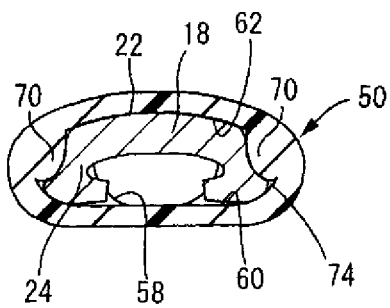
Figure 12C:
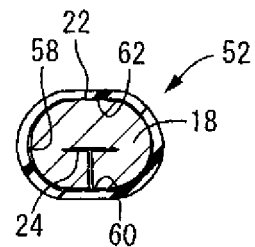
Figure 21:
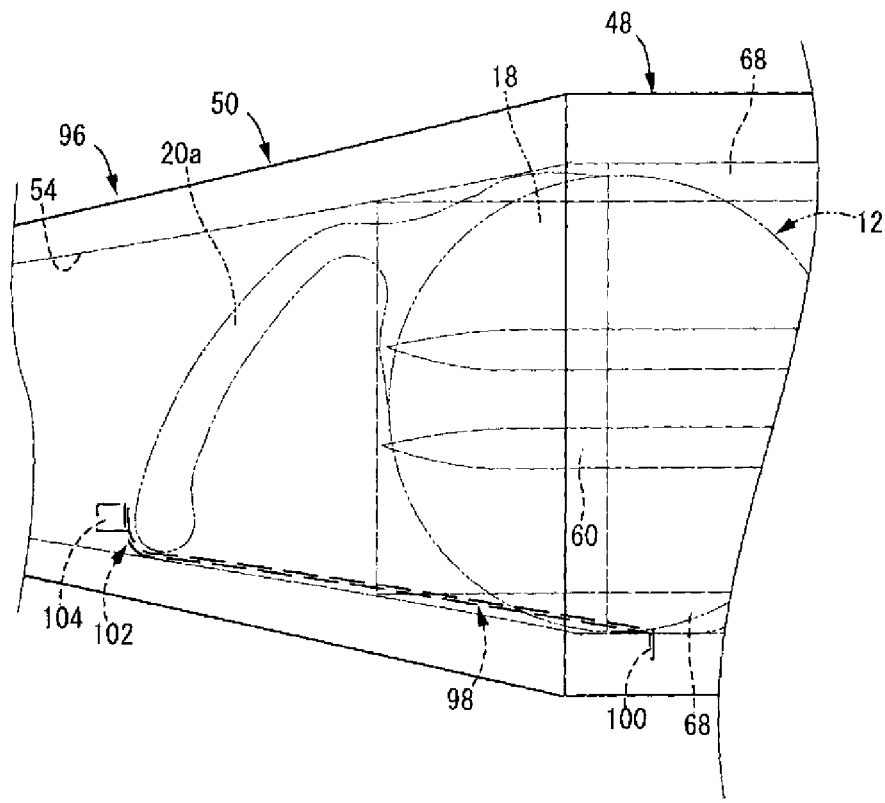
Figure 22:
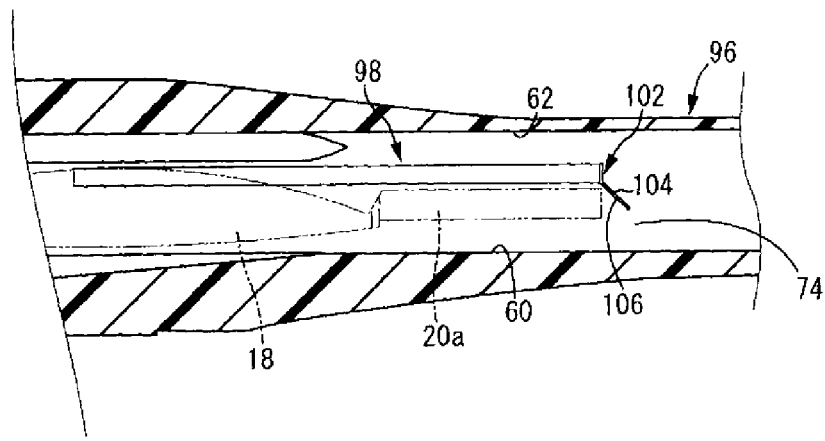
Figure 23:
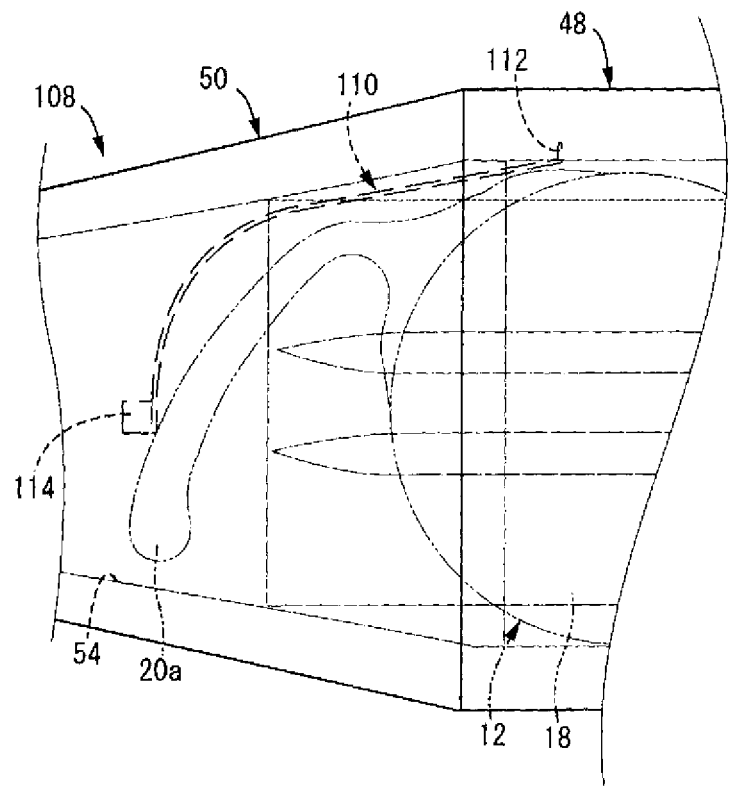
Figure 24:
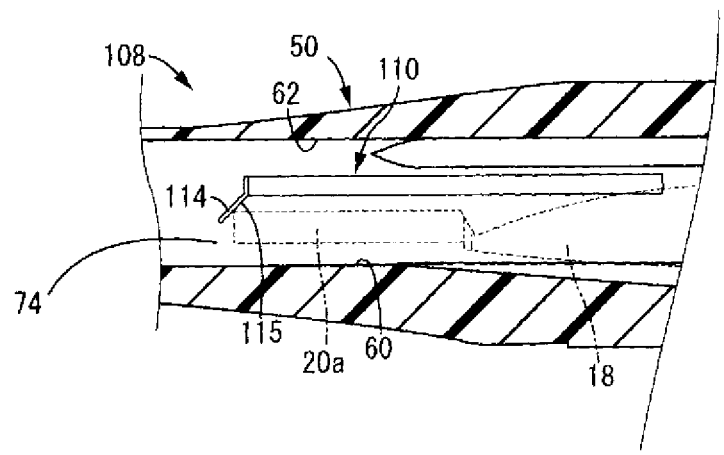
Figure 34:
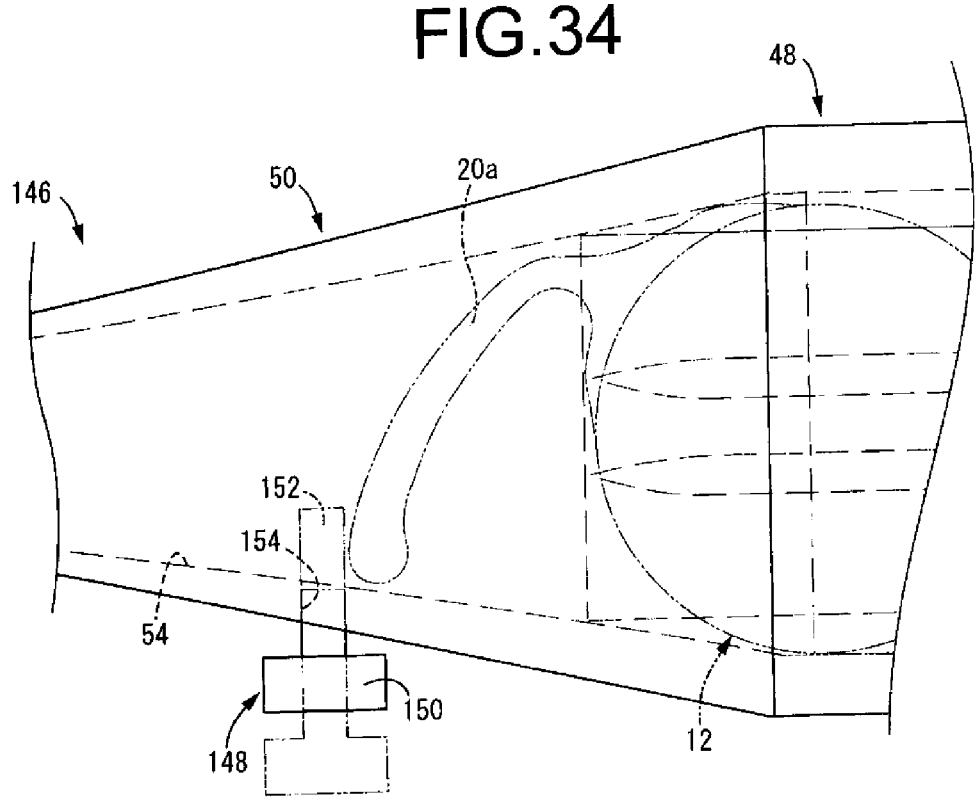
Figure 35:
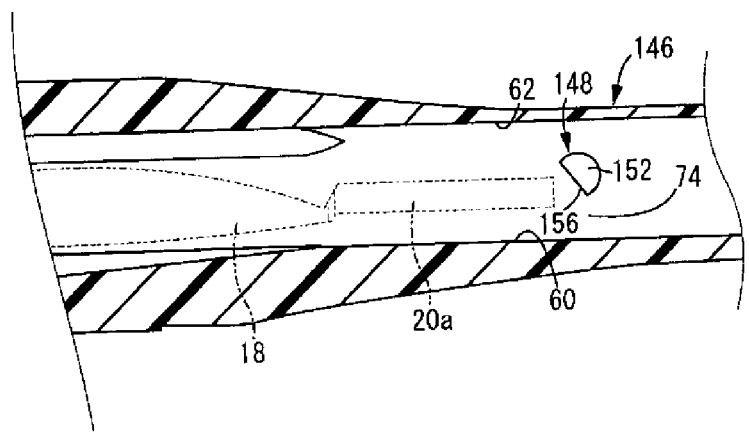

Next, we will describe the intraocular lens insertion device 146 as an eighth embodiment of the present invention based on FIG. 34 and FIG. 35. The intraocular lens insertion device 146 of this embodiment is provided with an entry contact member 148 as the interfering acting part instead of having the convex part (70) provided as compared with the intraocular lens insertion device (10) of the first embodiment.

The entry contact member 148 is formed by a synthetic resin material, rubber material or the like, and is constituted provided with an entry axis part 152 at one side in the thickness direction of a grasping part 150 which exhibits a thick-walled flat plate shape. This kind of entry contact member 148 is attached to the nozzle unit 46 in a state with the entry axis part 152 inserted through a through hole 154 formed opening at the top surface 62 piercing through the peripheral wall part of the middle part 50 in the width direction of the nozzle unit 46. In a state attached to the nozzle unit 46, the entry axis part 152 projects to one width direction side from the other width direction end part of the top surface 62. In this state, the entry axis part 152 is positioned further above than the bottom surface 60. By doing this, the specified gap 74 is formed between the entry axis part 152 and the bottom surface 60. Also, an interfering surface 156 given a tilt approaching the bottom surface 60 as it goes to the axial forward direction of the nozzle unit 46 is formed on the outer peripheral surface of the entry axis part 152.

As described above, in a state with the entry contact member 148 attached to the nozzle unit 46, the haptic 20*a* of the movement direction front side of the intraocular lens 12 moving within the nozzle unit 46 is in contact with the interfering surface 156 of the entry axis part 152. By doing this, external force is applied toward the movement direction back side on the haptic 20*a*, and the haptic 20*a* is displaced approaching the optical portion 18 side. At that time, the haptic 20*a* slides over the interfering surface 156 to the bottom surface 60 side. Once the haptic 20*a* is displaced approaching the optical portion 18 side, the entry axis part 152 is drawn into a position at which it does not project from the top surface 62 of the nozzle unit 46. After that, the intraocular lens 12 is extruded from the nozzle unit 46 in a state with the haptic 20*a* approaching the optical portion 18 side. As is clear from this, with this embodiment, the insertion tube part is constituted by the nozzle unit 46 to which the entry contact member 148 is attached.

Above, we gave a detailed description of embodiments of the present invention, but the present invention is not limited to those specific notations, For example, with the aforementioned embodiments, the support member 35 is removably attached to the stage 30 of the device main unit 14, the intraocular lens 12 is lifted up by the acting projections 36*a*, 36*a*, 36*b*, 36*b* of this support member 35, and is set in a state whereby contact on the optical portion 18 is avoided to the extent possible, but this kind of support member 35 is not essential for the present invention. In specific terms, it is also possible to directly place and set the intraocular lens 12 on the lens placement surface 34 of the stage 30 without providing the through holes 37*a*, 37*a*, 37*b*, 37*b* on the stage 30 of the device main unit 14 and without using the support member 35.

Also, when not using this support member 35, rather than providing this packaged in a state with the intraocular lens 12 set in advance, it is preferable to have the intraocular lens 12 unpacked with it having been packed separately from the intraocular lens insertion device 10, and to house and set it on the lens placement surface 34 of the stage 30 of the intraocular lens insertion device 10 at the time of surgery. By doing this, it is possible to avoid problems due to directly contact and application of stress by the lens placement surface 34 in relation to the optical portion 18 of the intraocular lens 12 over a long period in the course of storage and distribution.

Also, when using the support member 35 as well, it is possible to form the acting projections at positions that contact and support the optical portion 18 of the intraocular lens 12 or the middle part or the tip part or the like in the extending direction of the haptics 20*a*, 20*b*, for example.

The shape and constitution of the stage 30 and insertion tube part (nozzle unit 46) and the like of the device main unit 14 that determine the variation modes of the optical portion of the intraocular lens are set as appropriate according to the target shape that is deformed when inserting the intraocular lens into the eye, and are not limited to the notations of the embodiments, including whether or not to use the guide rails 66, 66 or the side rails 68, 68 or the like, for example. Specifically, modes for which there is deformation of the lens to be smaller when inserting the intraocular lens are not limited to the mountain fold state or the valley fold state as described above, and there are many varieties as is well known from the past, and in specific terms, it is possible to use a rounding deformation or the like by which the lens is wound up, and various constitutions known from the past can also be used with the intraocular lens insertion device of the present invention according to variation forms having that kind of purpose.

KEYS TO SYMBOLS

10: Intraocular lens insertion device, 12: Intraocular lens, 14: Device main unit, 16: Plunger, 18: Optical portion, 20*a*: haptic, 20*b*: haptic, 46: Nozzle unit (insertion tube part), 60: Bottom surface, 66: Guide rail (deformation guide member), 68: Side rail (deformation guide member), 70: Convex part (interfering acting part, engaging part), 72: Interfering surface, 98: Flexible locking piece, 118: Concave part, 128: Rough surface part, 132: Flexible projection, 138: Entry contact member

The invention claimed is:
1. An intraocular lens insertion device comprising:
a tube shaped device main unit configured to receive an intraocular lens having a pair of haptics projecting from an optical portion;
a plunger adapted to be inserted into the device main unit from a back side of the device main unit in an axial direction thereof, the plunger being attached to the device main unit;
a stage configured to receive the intraocular lens, the stage being provided at an intermediate part of the axial direction of the device main unit, the stage being arranged such that the intraocular lens is able to be placed flat on the stage, the pair of haptics facing from a front side and a back side of the optical portion relative to a movement direction of the plunger;
a tapered insertion tube part formed facing the front side in the axial direction from the stage so that the intraocular lens on the stage is insertable into an eye by being moved forward in the axial direction of the device main unit by the plunger and by being transformed to a smaller configuration and extruded through the insertion tube part; and
an interfering acting part that is provided in the insertion tube part and that is adapted to be in contact with a first one of the pair of haptics extended forward in the movement direction of the intraocular lens moved by the plunger, the interfering acting part being adapted to apply external force on the first haptic in a backward direction opposite to the forward movement direction, in order to curve and deform the first haptic toward the optical portion, wherein
the interfering acting part of the insertion tube part includes an engaging part formed at least at one side in a width direction of the insertion tube part and arranged to engage with the first haptic of the intraocular lens moving within the insertion tube part,
the engaging part has a convex part projecting above an inner surface of the insertion tube part at least at one side of the width direction, and
the convex part includes a flexible locking piece that is deformable in a direction for which a projection height of the flexible locking piece gets smaller above the inner surface of the insertion tube part opposite to a projection direction of the flexible locking piece above the inner surface of the insertion tube part.
2. The intraocular lens insertion device according to claim 1, further comprising:

a flat bottom surface extending from the stage at an opening part to a stage side of the insertion tube part, the convex part being formed at a position separated upward from the flat bottom surface at least at one side of the width direction of the flat bottom surface, and a gap provided closer to the bottom surface side than the convex part.

3. The intraocular lens insertion device according to claim 1, further comprising:

a deformation guide member in a hollow interior of the insertion tube part, the deformation guide member being configured to fold and deform the optical portion of the intraocular lens to a mountain shape or a valley shape wherein the optical portion is convex in an upward direction or a downward direction, respectively, using a ridge line or a valley line extending in the movement direction as the intraocular lens is moved within the insertion tube part, and a tilt on an interfering surface of the insertion tube part that interferes with the first haptic, the tilt tilting gradually toward a concave side that faces opposite a convex side of the optical portion deformed by the deformation guide member as the interfering surface moves forward in the movement direction of the intraocular lens, wherein, by guiding action of the tilt added to the interfering surface, the first haptic is deformed and guided to enter the concave side of the optical portion of the folded and deformed intraocular lens.

4. The intraocular lens insertion device according to claim 1, wherein the intraocular lens comprises a single piece with the pair of haptics being formed integrally with the optical portion.

5. An intraocular lens insertion device comprising:

a tube shaped device main unit configured to receive an intraocular lens having a pair of haptics projecting from an optical portion;

a plunger adapted to be inserted into the device main unit from a back side of the device main unit in an axial direction thereof, the plunger being attached to the device main unit;

a stage configured to receive the intraocular lens, the stage being provided at an intermediate part of the axial direction of the device main unit, the stage being arranged such that the intraocular lens is able to be placed flat on the stage, the pair of haptics facing from a front side and a back side of the optical portion relative to a movement direction of the plunger;

a tapered insertion tube part formed facing the front side in the axial direction from the stage so that the intraocular lens on the stage is insertable into an eye by being moved forward in the axial direction of the device main unit by the plunger and by being transformed to a smaller configuration and extruded through the insertion tube part; and an interfering acting part that is provided in the insertion tube part and that is adapted to be in contact with a first one of the pair of haptics extended forward in the movement direction of the intraocular lens moved by the plunger, the interfering acting part being adapted to apply external force on the first haptic in a backward direction opposite to the forward movement direction, in order to curve and deform the first haptic toward the optical portion, wherein the interfering acting part of the insertion tube part includes a flexible projection which is formed at least at one side of a height direction of the insertion tube part and is arranged to engage with the first haptic of the intraocular lens moving within the insertion tube part, and a projection volume of the flexible projection to the insertion tube part interior is made smaller by deformation after engagement with the first haptic, thereby allowing passage of the optical portion of the intraocular lens.

\* \* \* \* \*

UNITED STATES PATENT AND TRADEMARK OFFICE
CERTIFICATE OF CORRECTION

Page 1 of 7

PATENT NO. : 9,072,601 B2
APPLICATION NO. : 13/502637
DATED : July 7, 2015
INVENTOR(S) : Tanaka et al.

It is certified that error appears in the above-identified patent and that said Letters Patent is hereby corrected as shown below:

Delete the title page and substitute therefore with the attached title page consisting of the corrected illustrative figure(s).

Please replace FIGS. 7, 12A, 12B, 12C, 21, 22, 23, 24, 29, 34 and 35 with FIGS. 7, 12A, 12B, 12C, 21, 22, 23, 24, 29, 34 and 35 as shown on the attached pages.

Signed and Sealed this
Twenty-fourth Day of May, 2016

Michelle K. Lee
*Director of the United States Patent and Trademark Office*

(12) United States Patent
Tanaka et al.

(10) Patent No.: US 9,072,601 B2
(45) Date of Patent: Jul. 7, 2015

(54) INTRAOCULAR LENS INSERTION DEVICE

(75) Inventors: Masayoshi Tanaka, Nagoya (JP);
Kazuharu Niwa, Nagoya (JP);
Yasuhiko Suzuki, Hashima-gun (JP)

(73) Assignee: KOWA COMPANY, LTD., Nagoya (JP)

(*) Notice: Subject to any disclaimer, the term of this patent is extended or adjusted under 35 U.S.C. 154(b) by 449 days.

(21) Appl. No.: 13/502,637

(22) PCT Filed: Oct. 22, 2009

(86) PCT No.: PCT/JP2009/005546
§ 371 (c)(1),
(2), (4) Date: May 7, 2012

(87) PCT Pub. No.: WO2011/048631
PCT Pub. Date: Apr. 28, 2011

(65) Prior Publication Data
US 2012/0221102 A1 Aug. 30, 2012

(51) Int. Cl.
*A61F 2/16* (2006.01)
*A61F 2/14* (2006.01)

(52) U.S. Cl.
CPC .. *A61F 2/167* (2013.01); *A61F 2/16* (2013.01); *A61F 2/1648* (2013.01); *A61F 2/1662* (2013.01); *A61F 2/143* (2013.01); *A61F 2002/1681* (2013.01)

(58) Field of Classification Search
CPC ............. A61F 2/16; A61F 2/1648; A61F 2/1662 2/1678; A61F 2/1691; A61F 2/143; A61F 2002/1681
See application file for complete search history.

(56) References Cited

U.S. PATENT DOCUMENTS

| | | | |
|---|---|---|---|
| 6,491,697 B1* | 12/2002 | Clark et al. | 606/107 |
| 7,037,312 B2* | 5/2006 | Kikuchi et al. | 606/107 |
| 7,156,854 B2 | 1/2007 | Brown et al. | |

(Continued)

FOREIGN PATENT DOCUMENTS

| | | |
|---|---|---|
| CN | 101467925 A | 7/2009 |
| EP | 2 298 242 A1 | 3/2011 |

(Continued)

OTHER PUBLICATIONS

Jan. 26, 2010 International Search Report issued in International Patent Application No. PCT/JP2009/005546 (with translation).

(Continued)

*Primary Examiner* — Jonathan W Miles
*Assistant Examiner* — Todd J Scherbel
(74) *Attorney, Agent, or Firm* — OBIT PLC

(57) ABSTRACT

An intraocular lens insertion device having a novel configuration, capable of more accurately arranging front and back surfaces of an intraocular lens in a proper direction. The intraocular lens insertion device is adapted in such a manner that the intraocular lens is set on a stage in a state placed flat with a pair of haptics extended facing front and back sides in a movement direction by a plunger. Also, an interfering acting part is provided to an insertion tube part, and the interfering acting part interferes with the haptic, which is extended facing the front side in the movement direction of the intraocular lens moved by the plunger, to apply on the haptic an external force toward the back side in the movement direction. Thus, the interfering acting part curves and deforms the haptic to a side approaching an optical portion.

5 Claims, 22 Drawing Sheets

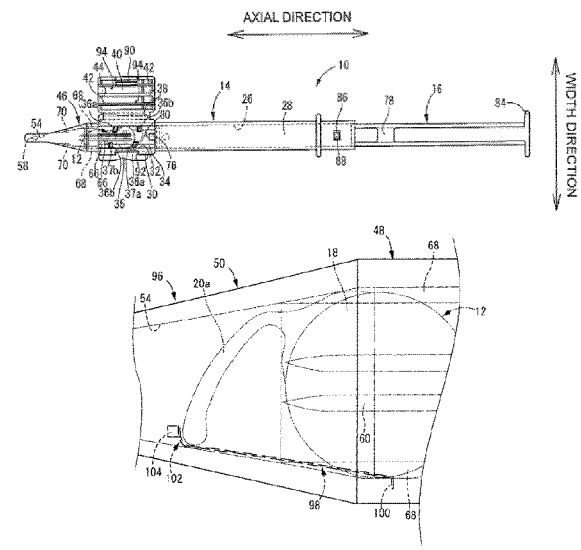

FIG.7
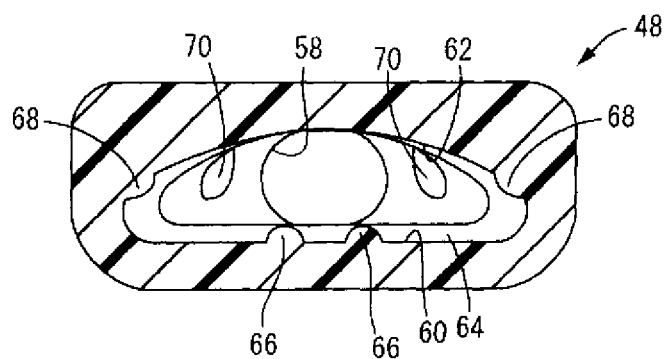
A—A
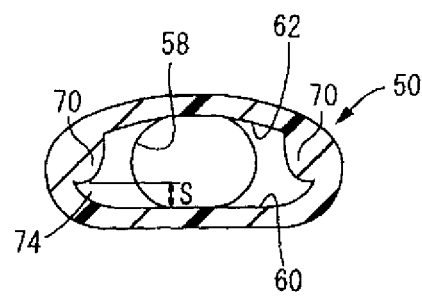
B—B
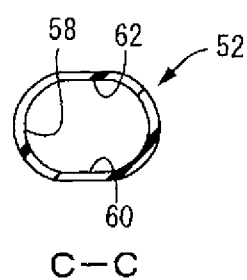
C—C